United States Patent [19]

Kude et al.

[11] 4,444,337

[45] Apr. 24, 1984

[54] APPARATUS FOR PROPORTIONING FLUIDS

[75] Inventors: William B. Kude, Plymouth; A. Noel J. Pearman; Daniel L. Youngbauer, both of St. Paul, all of Minn.

[73] Assignee: Honeywell Inc., Minneapolis, Minn.

[21] Appl. No.: 271,477

[22] Filed: Jun. 8, 1981

Related U.S. Application Data

[62] Division of Ser. No. 105,794, Dec. 20, 1979, abandoned.

[51] Int. Cl.³ .......................... G01N 27/26; B01F 3/02
[52] U.S. Cl. ..................................... 222/139; 222/330; 222/370; 48/180 P; 137/624.15; 137/625.12; 366/160; 366/302; 366/316; 366/321
[58] Field of Search ............... 366/160, 302, 316, 321; 137/624.15, 624.20, 625.12, 625.15, 625.31; 48/180 P; 431/354; 123/590, 591, 593; 222/370, 139, 330

[56] References Cited

U.S. PATENT DOCUMENTS 3,494,175 2/1970 Cusik et al. ................ 137/625.12 X

OTHER PUBLICATIONS

Hadley et al., "Design, Construction, and Testing of a Commercial Prototype Disc Diluter", EPA Contract No. 68-02-0716, EPA Document No. EPA-650/2-74-055, Jul. 1974.

Primary Examiner—David A. Scherbel
Attorney, Agent, or Firm—Charles G. Mersereau

[57] ABSTRACT

An apparatus and method for determining the heating value of gaseous fuels is disclosed which include the novel means for establishing a mixture of air and the gaseous fuel of interest in known volumetric proportions. An electrochemical sensor is provided to sense the products of combustion of the precise volumetric mixture and the output of the sensor is indicative of the relation of the mixture to a stoichiometric mixture of fuel and air. This system is provided for adjusting the proportions of fuel and air in the mixture of interest in response to the output of the electrochemical sensor until the sensor indicates that the mixture of known proportions is substantially stoichiometric. The system is provided for determining the heating value of the fuel from a known relationship between the heating value of the constituents of the fuel and the amount of oxygen required for stoichiometric combustion.

13 Claims, 28 Drawing Figures

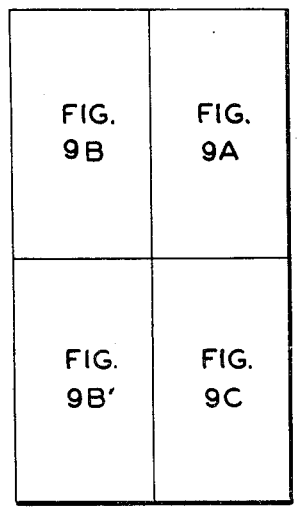
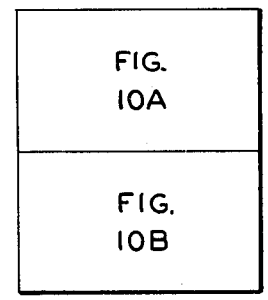
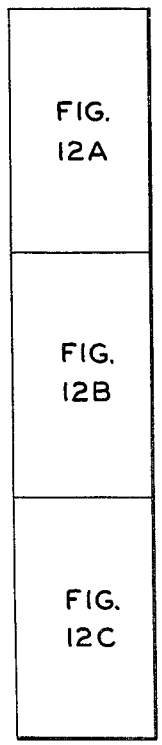
FIG. 8

TYPICAL ELECTROCHEMICAL SENSOR RESPONSE

F/G. 18

APPARATUS FOR PROPORTIONING FLUIDS

This is a division of application Ser. No. 105,794, filed Dec. 20, 1979, abandoned in favor of application Ser. No. 331,431, filed Dec. 16, 1981 and now U.S. Pat. No. 4,386,858.

BACKGROUND OF THE INVENTION

1. Field of the Invention

The present invention relates generally to the field of measuring and monitoring the heating value of gaseous fuels such as natural gas and, more particularly, to a method and apparatus for determining the heating content or calorific value of such fuels from a determination substantially at the stoichiometric point of combustion of unknown mixtures containing precise volumetric proportions of fuel and air.

2. Description of the Prior Art

The heating value of gaseous fuels such as natural gas are frequently given assumed average numbers. Thus, the heating value of natural gas, for example, is frequently assumed to be 1000 British thermal units (BTU's) per cubic foot. In the past, pricing of such fuels has been based upon either the assumption of a nominal average value or the periodic checking of the actual value by a variety of time-consuming methods.

In one method chromatographic analysis of the constituents has been used to compute the actual heating value or BTU content of a given natural gas from the percentage composition of the mixture. In another method, the heat content has been determined by measuring the amount of heat liberated in burning exactly one cubic foot of gas (saturated with water) at standard conditions of temperature and pressure. The heat so liberated is absorbed by a weighed amount of water and the subsequent temperature rise of the water used to calculate the "gross or (higher) heating value." This "calorimeter bomb" approach, like the chromatographic approach, has several drawbacks.

Both methods involve reasonably expensive instrumentation and require considerable labor to perform the measurements and calculations. Such testing also, of necessity, introduces considerable time delay and certainly appears less desirable than an on-line system. Even so, these might be sufficient methods if, in fact, the composition of the gas being used did not vary greatly with time. However, the composition of natural gas, for example, may vary greatly in composition depending on the gas field from which it came and the treatment it receives before distribution. The gas that reaches the customer or consumer is frequently only about 85 percent methane with the remaining 15 percent being a mixture of various hydrocarbon molecules such as ethane, propane, n-butane, i-butane, etc. Also, as much as 25 percent of the gas reaching the customer may be made up of non-combustible constituents which occur naturally or have been added to the mixture. These include nitrogen, air, and carbon dioxide. Natural gas is used herein as a representative example because it is by far the most widely used gaseous fuel.

The inerts, of course, add nothing to the heating value, and the heating value of alkane and other hydrocarbons of a higher order than methane have a higher heating value on a volumetric basis because of their higher molecular weights. In view of the great variation in constituents of natural gas, the heating value even in a single distribution system may vary greatly with time.

In addition to the other variations, numerous gas utilities have found that in severe winter weather it is cost justified to add a mixture of propane and air to the fuel in order to meet peak demand. They have found that the increased cost of propane at such peak load periods is less than the cost of additional distribution capacity which would otherwise be necessary to meet the peak loads with gas that cannot be stored as liquid adjacent to users.

As a result of all these factors, a random sampling of the heat content of the natural gas being distributed, might lead to great inaccuracies as to the actual heating value of the fuel delivered. Thus, it is necessary for the heat content of the natural gas to be continually monitored and adjusted in order to stay within promised specified limits and to assure that the user is charged for the proper amount of heating value he receives from the fuel.

Other incentives are involved in the desirability for providing an efficient on-line device for monitoring the heating value of gas. Users, especially those in industries, which require large amounts of gas for heat processing equipment can utilize such data to adjust gas input modes to provide a more uniform total heat input. They can also utilize such information to adjust burner controls so as to provide the proper air-fuel ratio and thereby avoid inefficiencies which occur when the burners are operating at a ratio which is either too lean or too rich.

Attempts have been made to provide "on-line" devices. In the prior art it is generally known that the heat content of a gaseous fuel such as natural gas is related to the ratio of fuel to air necessary for complete combustion of the gas. One prior art device utilizes a system in which the heat content of the fuel is related mathematically to that ratio of air to fuel which maximizes the adiabatic flame temperature of the mixture. In that system the air and fuel are split between two burners in such a way that the mixture in one burner has a slightly higher air-fuel ratio than the other. The air flow is allowed to remain constant, and the fuel flow is varied in the two burners until the temperature of both flames is the same. In this manner, one burner approaches the maximum flame temperature from the "rich" side and the other from the "lean" side. The fuel flow is metered as by a turbine meter, and, based on the metered rates of air and fuel, a BTU heat content is calculated assuming the maximum adiabatic flame temperature occurs at the stoichiometric point of the combustion mixture. Actually, the maximum flame temperature may be reached when the mixture is somewhat lean, i.e. when an amount of excess air is present.

A prior art method of calculating the heat content from such measurements is found in "New Approach to the Continuous Measurement of Calorific Values of Gaseous Fuels" by William H. Clingman, Jr., *AGA Operating Section* (1972). That system has the drawback that it requires both accurate fuel measurement and temperature measurement of two complete burner systems for comparison.

The use of electrochemical cells as oxygen or combustibles sensors to sense the residual products of combustion including electrochemical cells based on ceramic compounds such as $ZrO_2$ is also known. Under normal conditions, natural gas is burned with an excess of oxygen to assure complete combustion and an absence of carbon monoxide in the products of combustion. This leads to the presence of an amount of excess oxygen after combustion which raises the possibility that an oxygen sensor based on zirconia or the like could provide a relatively inexpensive and rapid solution to the problem of determining heating values for natural gas mixtures based on the air-fuel ratio. Such solid electrolyte-based oxygen sensors have been used to rapidly provide information for such systems as catalytic automobile exhaust control. Several different types of solid electrolyte-based oxygen sensors are commercially available.

Thus it has been proposed to use a ceramic based electrochemical made chiefly of zirconia ($ZrO_2$) which is known to exhibit a Nerstian voltage output when exposed to differing partial pressures of oxygen on each side of the ceramic material. This can be used to sense the amount of oxygen present in the products of combustion. That system proposes to utilize a known mass ratio between the fuel and oxygen supplied to a burner in conjunction with the measurement of excess oxygen after combustion using the Nernstian relationship to provide a basis for deriving the heat content of the fuel. According to that system, measurements should be made when the combustion mixture contains about 20 percent excess air, that is, not stoichiometric combustion.

That system requires that the air and fuel be controlled so as to be measured in relation to standard temperature and pressure and precise metering of the mass flows of fuel and air. Also the sensor output is decidedly temperature sensitive in the presence of more than minute amounts of oxygen. Thus, when operating in the oxygen-rich portion of the $ZrO_2$ electrochemical response curve, the temperature of the sensor must be carefully controlled. Unfortunately, the system does not take into consideration the fact that as the heating value of the gas to be measured increases, so does the average molecular weight of the gas. While this could be overcome with appropriate correction factors, if only combustible gases were involved, the molecular weight of the fuel species can also be varied because of the presence of inert species in the mixture which leads to calculation errors.

SUMMARY OF THE INVENTION

According to the present invention, the problems associated with prior art attempts at on-line measurement of the heat content of gaseous fuel are substantially solved by the provision of a unique heat content measuring system which utilizes a ceramic electrochemical oxygen sensor in a manner which eliminates both the need for precise temperature control of the sensor and errors introduced by inert constituents. The heat content measuring system of the present invention includes an accurate volumetric measuring system to accurately proportion the fuel which is mixed with air. A single sample burner in combination with the sensing system provides the necessary air-fuel information necessary to the heat content measurement of the fuel gas of interest. The system is designated to control combustion at the stoichiometric point (FIG. 18) wherein the electrochemical sensor exhibits a step-change function to produce increased accuracy. At this point, the precise volumetric ratio of fuel to air is accurately known from the measuring system and the heat content of the fuel can be accurately determined from that ratio in a manner simplified by the elimination of the effects of several undesirable variables.

The fuel heat content metering system of the present invention includes a precise, adjustable metering system which accurately proportions an amount of fuel gas or calibration gas to be tested with a known amount of air such that at any given time, the volumetric ratio of air, and therefore, to fuel is precisely known. The mixture is fed to a burner system in which the fuel is combusted in the presence of a solid state ceramic electrochemical cell which provides a step-change in voltage output as the amount of residual oxygen or combustibles approaches zero, that is, approaches the point of stoichiometry. An electrical signal from the electrochemical cell is utilized with a programmable electronic processing system to adjust the fuel mixture in accordance with the output of the electrochemical cell to achieve and determine the stoichiometric air-fuel ratio as signalled by the rapid change in electrical output of the cell at that point. The air-fuel ratio at that point is known from the measuring system and the heat content of the fuel is readily determined therefrom.

In the preferred embodiment, the metering of the fuel and air is accomplished by one of several alternate, novel systems which provide precise, time proportioning volumetric measurement. In one embodiment of the proportioning system of the invention, fuel and air are fed through a rotary valve system in which the proportion of air or gas transferred therethrough to the combustion chamber depends on the speed of rotation of the rotary valve. The rotating member contains hollow chambers which are alternately filled with fuel and purged with air as they are rotated in the fashion of a Gatling gun. The air flow remains constant and the fuel introduced varies with the angular speed of the rotor. A motor, the speed of which can accurately be controlled, as with a stepping motor, is provided to allow for a great deal of flexibility in adjusting the rotation speed and thus the air-fuel ratio.

In an alternate embodiment of a proportioning system, fuel is fed to a mixing chamber alternately through each of two separate series of valves such that precise known amount of fuel contained in a cylindrical chamber between two valves in each series is ultimately pushed into the mixing chamber by a constant regulated air flow. While one series is connected to the burner, the cylindrical chamber of the other series is being refilled with the fuel gas. The system is switched in a time sequenced manner to alternately connect one valve series then the other to the measuring burner system. The air-fuel ratio is readily varied merely by adjusting the cycle time of the system.

Inasmuch as fuel and air are fed to the measuring burner at the same regulated pressure and, if packaged together, will be at or close to the same temperature, this eliminates the additional variables relating to differences in temperature and pressure which otherwise would have to be compensated by measuring the temperature and pressure and adjusting the calculation therefor. Temperature and pressure compensation, of course, may be provided in the fuel and air supply for applications wherein the keeping of equal pressure and temperature is not practicable.

Because precise volumetric measuring is used, the need for compensating for changes in molecular weights of combustibles or for the addition of inert components is also eliminated. Calculation of heat content is made utilizing a microprocessor system from a simplified known constant relationship between the air-fuel ratio at the stoichiometric point which is known from the speed of the sampling system and the corresponding fuel heat content. The results may be recorded or displayed in any manner desired.

The heat given off by the combustion of the given mixture can also be utilized to maintain the temperature of the electrochemical cell within the desired range. In the preferred embodiment, the cell within the desired range is a ceramic cell primarily made up of $ZrO_2$ stabilized with an amount of CaO, MgO, or $Y_2O_3$, to stabilize its temperature related response such that in the step-change portion of the sensing curve, the cell is repeatably accurate without temperature compensation from about 600° F. to 1,400° F.

BRIEF DESCRIPTION OF THE DRAWINGS

In the drawings wherein like numerals are used to designate like parts throughout the same:

FIG. 5A is a detail of a part of FIG. 5 rotated 180°;

FIG. 7A is a detail of a part of FIG. 7 rotated 180°;

FIG. 8 depicts the layout of the multi-sheet FIG. 9 which includes Parts 9A, 9B, 9B' and 9C, 10, 12, and 14.

DESCRIPTION OF THE PREFERRED EMBODIMENT

The heat content measuring system of the present invention contemplates a simple, accurate method and apparatus for determining the precise ratio of air to fuel in a combustible mixture which can be utilized, in turn, to accurately determine the heat content of the fuel used. This sytem does not require remote sampling and can actually be used in an on-line manner. As will be seen from the detailed description, substantially all of the sources of error introduced in previous attempts to achieve accurate on-line readings have been substantially eliminated.

Figure 1:
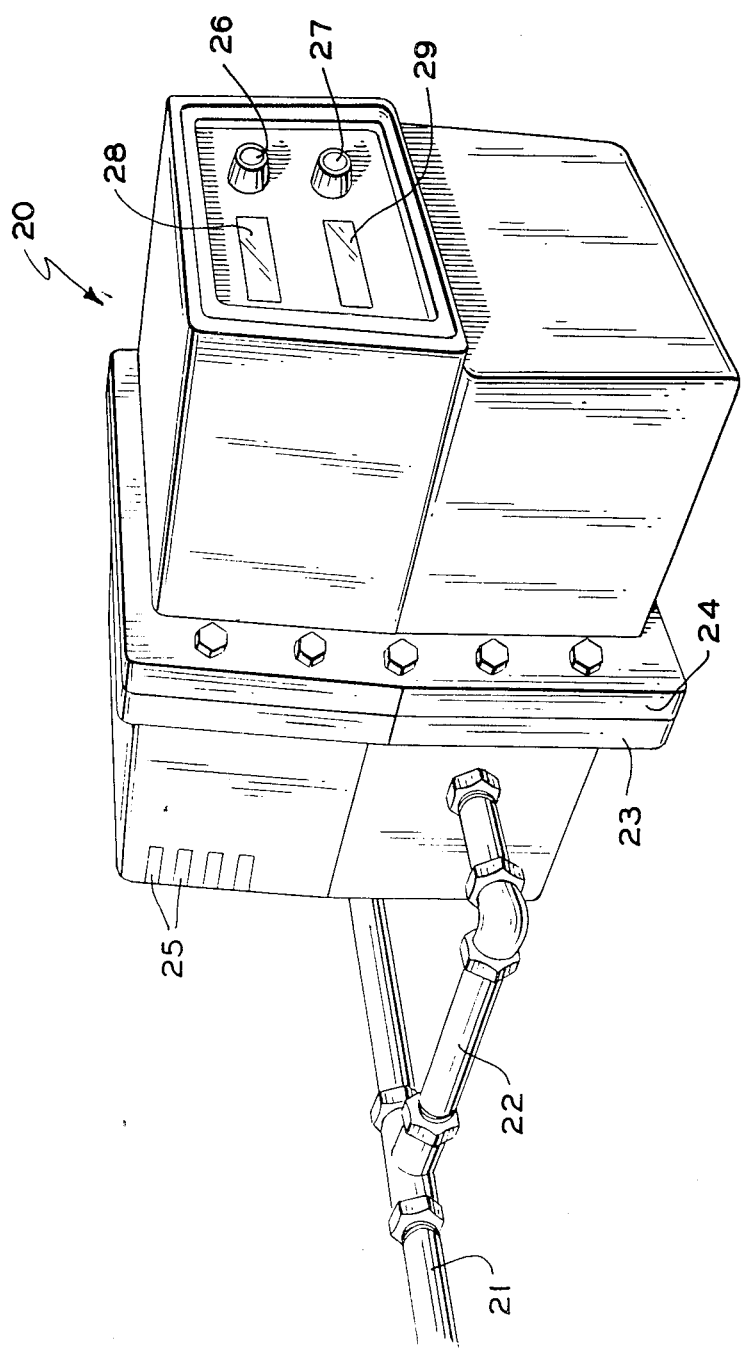
FIG. 1 is a perspective view of a mounted in-line instrument utilizing the invention.

In FIG. 1, there is shown generally at 20 an in situ placement of a heat content measuring device in accordance with the present invention. Thus, the device can be mounted on a fuel line 21 and connected to it by a sample line 22 such that continual on-line measuring of the fuel passing through the line 22 can be achieved. As depicted in FIG. 1, the apparatus may have an explosion proof case having halves 23 and 24 securely bolted together. Venting is provided as at 25. Typical adjustment knobs 26 and 27 corresponding to display readouts 28 and 29 are represented which may read out directly in air-fuel ratio, BTUs, or calories, or any other convenient units of measurement.

Figure 2:
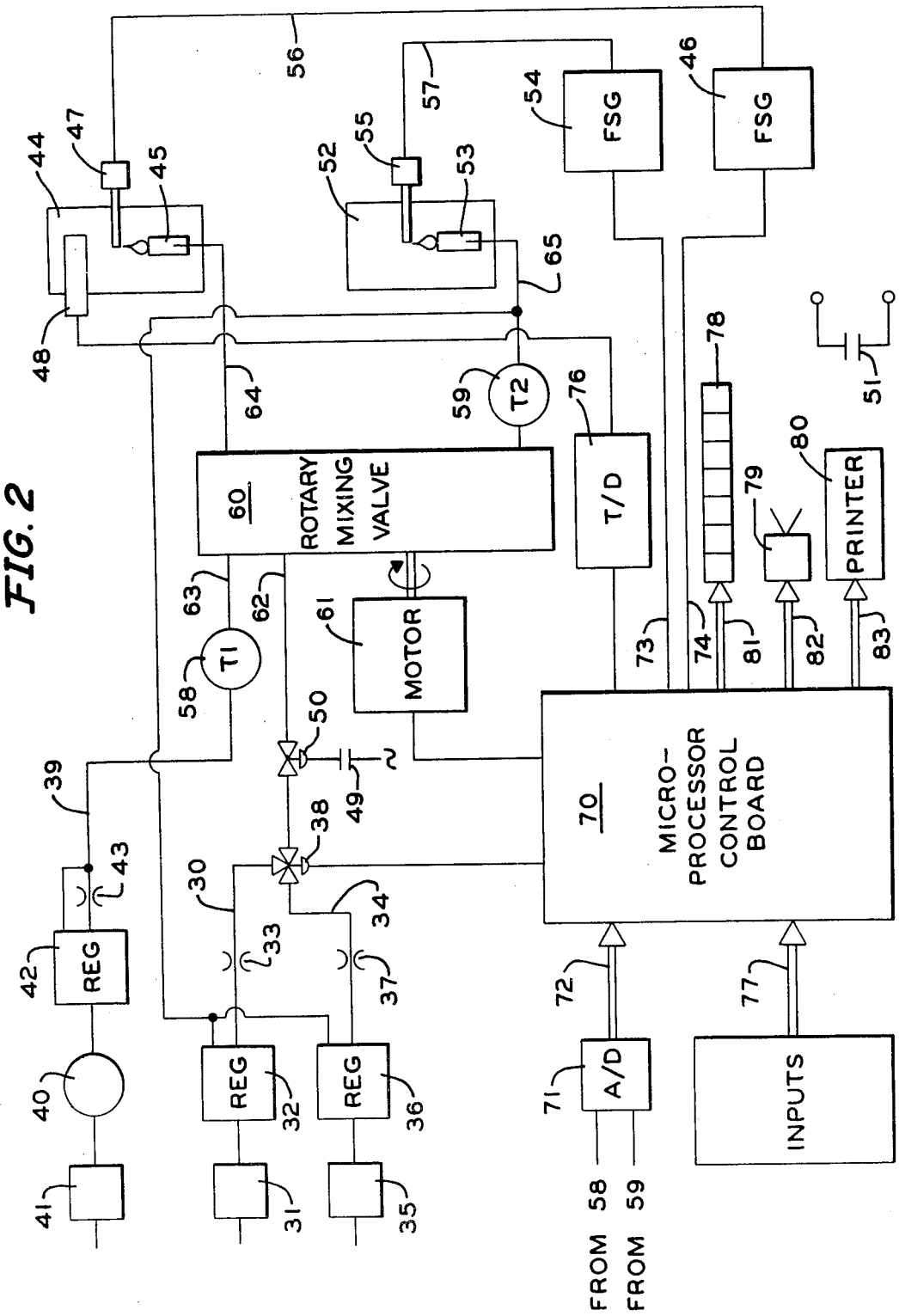
FIG. 2 is a schematic block diagram of the preferred embodiment of the invention.
Figure 3:
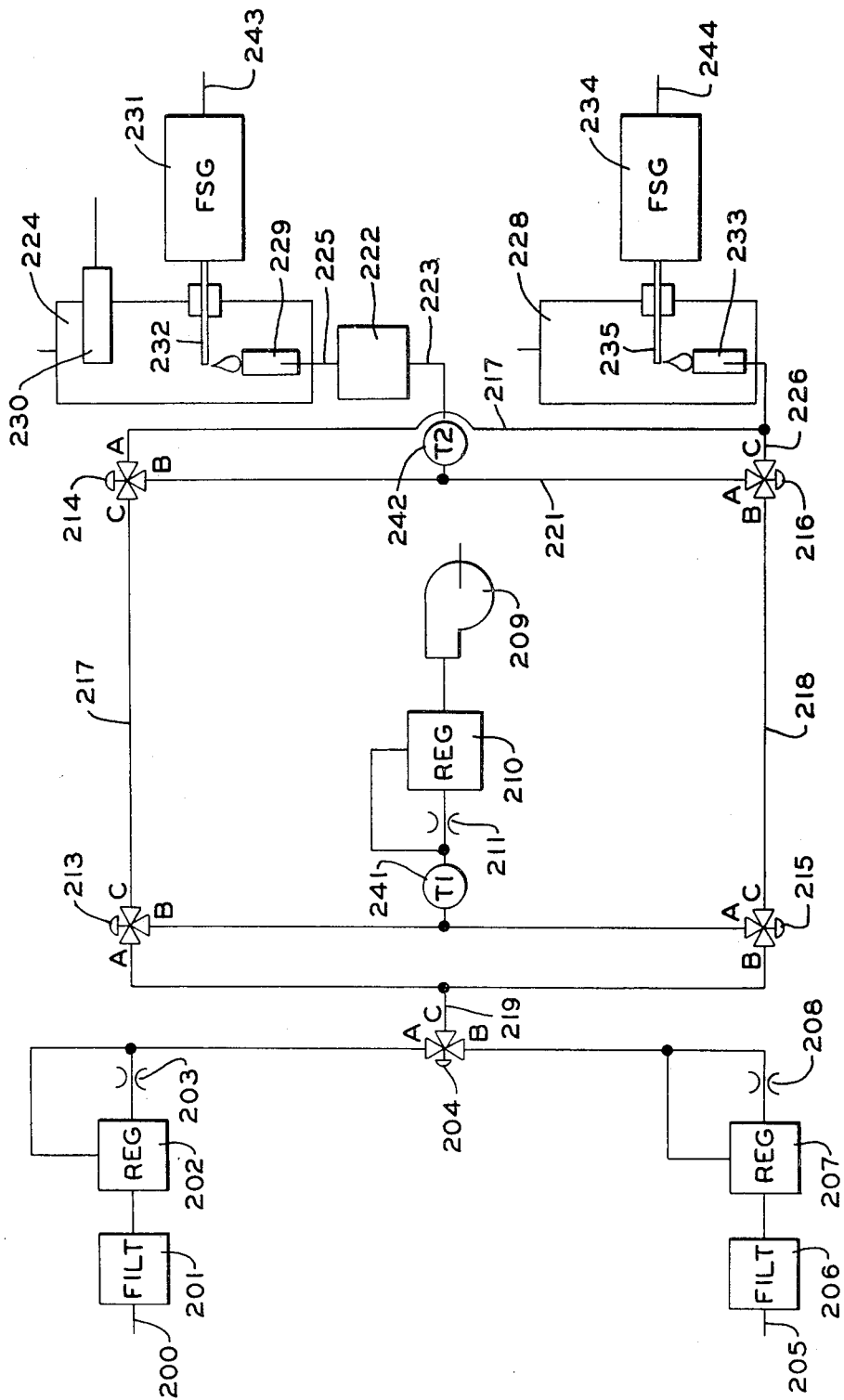
FIG. 3 is a schematic block diagram of an alternate embodiment of the invention.

FIGS. 2 and 3 depict alternate embodiments of the heat content measuring system of the invention. The system of FIG. 2 includes an air supply system, both calibration and unknown or sample gas supply systems, a mixing system or proportioning system, and a combustion and measuring system. In FIG. 3 there is shown an alternate embodiment to the system of FIG. 2 in which an alternate type of proportioning system is utilized.

The preferred embodiment is shown in FIG. 2. This includes an inlet sample fuel gas line 30 which includes corresponding filter 31, pressure regulator 32, and orifice 33, and, similarly, for the calibration gas system there is an inlet line 34, filter 35, regulator 36, and metering orifice 37. The lines 30 and 34 converge upon a three-way value 38. Similarly, air is provided in line 39 by blower 40 with filter 41, associated pressure regulator 42 and metering orifice 43. A sample or main combustion chamber is provided at 44 with burner 45, flame safeguard unit 46 with associated flame igniter-sensor 47 and the electrochemical combustion product sensor 48. Contact 49 associated with the main safety shutoff valve 50 is provided to shut off the fuel flow should a flame out or other problem occur. Similarly, an auxiliary contact 51 is provided for external use, also controlled by the main burner flame safeguard system 46. A flare and vent system is provided with combustion chamber 52, burner 53, flame safeguard unit 54 with its associated igniter-sensor 55. The main and flare combustion chambers are connected to their associated flame safeguard systems by conductors 56 and 57 respectively. The lines 56 and 57 also represent 16 conductor for the spark ignition in this schematic drawing.

Additional components include an air temperature sensor $T_1$ and fuel mixture temperature sensor $T_2$ with respective associated leads 58 and 59.

The embodiment of FIG. 2 introduces a completely distinct and unique proportioning and mixing concept including a rotary mixing valve 60 driven by an associated motor 61. The rotary valve is supplied by the gas of interest by line 62, and air by line 63. The proportional mixture is conveyed to the main burner by 64 and residual fuel to the vent burner by 65. The operation and details of the mixing system 60 and associated motor 61 will be described in greater detail with reference to the alternate embodiments thereof shown in FIGS. 4-9.

The main electrical components which will be described below are shown in block form in FIG. 2 and include a conventional microprocessor control board 70. Temperature information on lines 58 and 59 is processed by an analog-to-digital converter 71 and supplied to the control board by 72. Flame safeguard information is received on lines 73 and 74 and information from the sensor 48 on line 75 via a threshold detector 76. Various other inputs are received at 77. A display 78, alarm 79, and printer 80 receive information from the board 70 along respective routes 81, 82, and 83.

Figure 4:
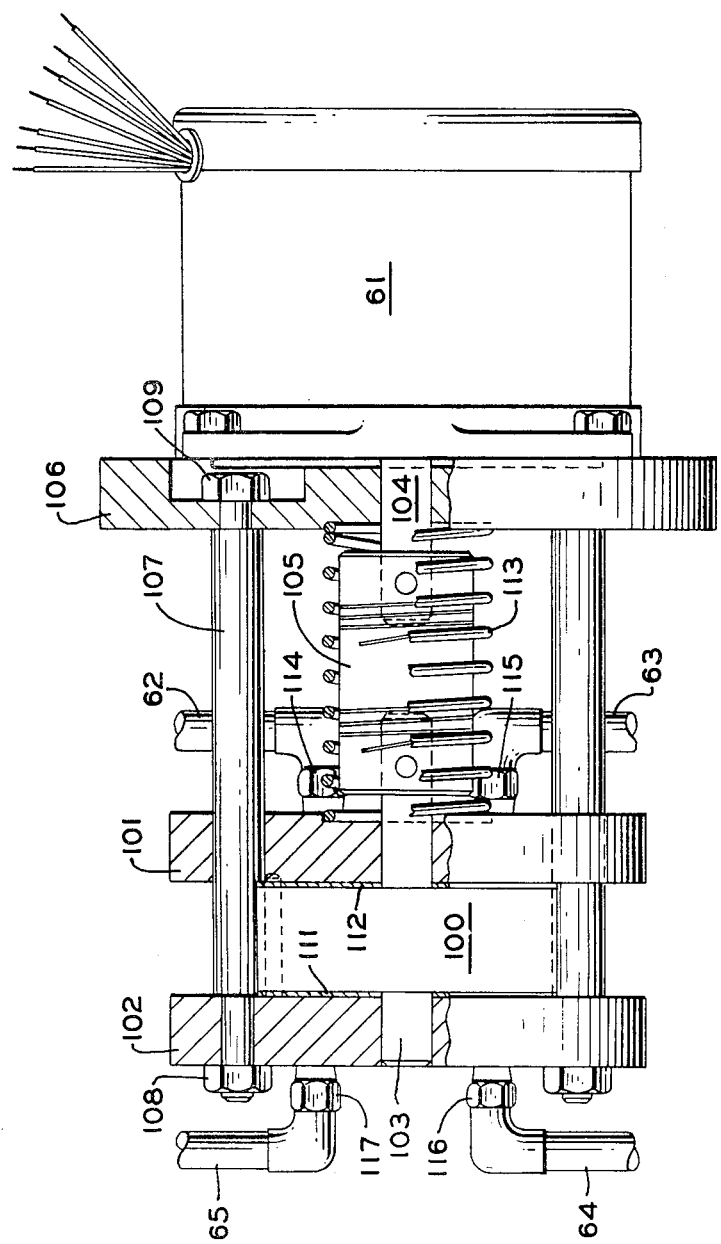
FIG. 4 is an view partially in section of a rotary valve system of the embodiment of FIG. 2.

In FIG. 4 there is pictured one embodiment of a rotary valve proportioning system in accordance with 60 of FIG. 2. The internal structure of the system is depicted in greater detail in the exploded view of FIG. 5. The basic components of the rotary valve system include the motor 61, the proportioning distribution rotor 100 flanked by a distribution plate 101 and an end plate 102. The shaft 103 of the rotor 100 is coupled to the shaft 104 of the motor 61 as by a flexible coupling 105. The end plate 102 is spaced from the motor mounting face plate 106 and secured thereto as by a plurality of radially distributed bolts 107 secured as by nuts 108 and 109. As can more adequately be seen in FIG. 5, the threaded bolts 107 are of such a diameter as to pass through holes 110 in the member 101 such that the plate member 101 is free to slide along the axes of bolts 107. The rotor member 100 is provided with flanking seals 111 and 112 and the entire assembly including the rotor 100, distribution plate 101, and end plate 102 with the seals 111 and 112 is held in place as by a helical spring 113 which pushes on the members 101 and 106 to hold member 101 in position at the desired pressure. The fuel inlet line 62 and air inlet line 63 are connected to the member 101 as by fitting at 114 and 115, respectively. The mixture to be combusted or vented leaves the mixing system as via fittings 116 and 117 connecting lines 64 and 65.

Figure 5:
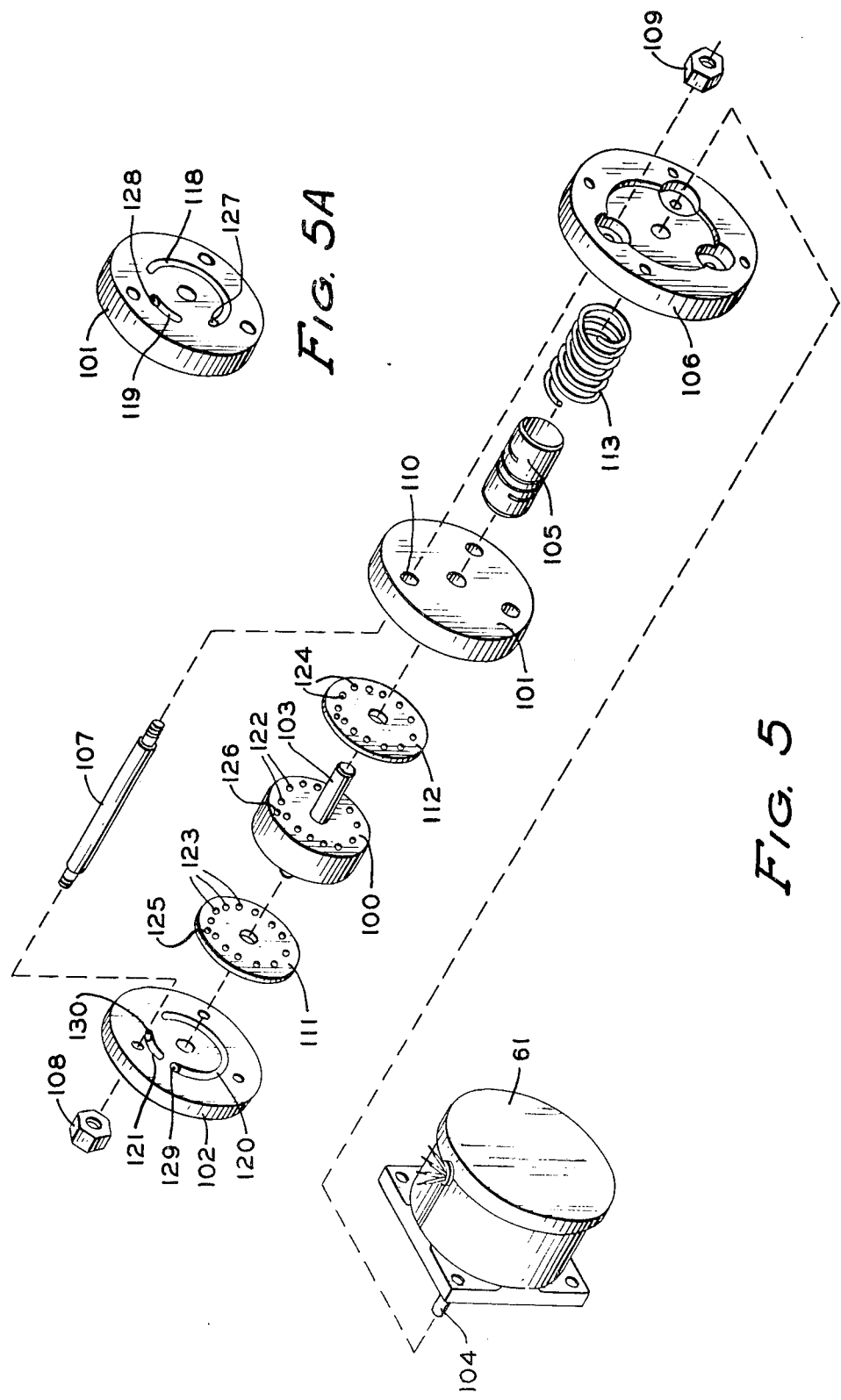
FIG. 5 is a reduced, exploded view of the rotary valving system of FIG. 4.

By means of the rotary mixing system depicted in FIGS. 4 and 5, air and fuel entering the system is precisely proportional in a unique manner. As seen in FIG. 5, the distribution member 101 is provided with an elongated partial annular groove or slot 118 and a shorter partial annular groove or slot 119. Both slots 118 and 119 may be of square section or semicircular section as desired. (It should be noted that the single member 101 in FIG. 5 has been flipped over or rotated 180° with respect to the other members of the exploded view to expose the internal slotted or grooved structure of the member). Corresponding grooves 120 and 121 are provided in the member 102. The rotor member 100 is provided with a symmetrical pattern of radially distributed holes 122 which cylinders of known volume extending through the member 100, and the seal members 111 and 112 are provided with a similar pattern of holes designated 123 and 124, respectively. Seals 111 and 112 are provided with a series of alignment holes as at 125 which fit over machined pegs as at 126 in the rotor member 100 to assure proper alignment of the seals with the rotor 100 such that the patterns of holes are aligned internally to connect the grooves 118 and 119 with the grooves 120 and 121, respectively. Inlet holes or parts 127 and 128 connect the grooves 118 and 119 with the respective air and fuel inlets at 115 and 114. Outlet holes or parts 129 and 130 connect with outlets 116 and 117, respectively in a like manner.

In this manner, the fuel in line 62 passes into the groove 119 and the air from conduit 63 passes into the groove 118. Thus, the groove 119 at all times is open to incoming fuel, and the groove 118 at all times is open to incoming air. When the motor 61 is energized, the rotor 100 and associated seals 111 and 112 are rotated with the motor shaft speed. This causes the hole systems of the rotor member 100 to alternately be exposed to the fuel of groove 119 and air of groove 118. The grooves 120 and 121 with associated outlet ports 129 and 130 therein are always connected respectively to the mixture outlet lines 64 and 65.

In operation, amounts of regulated air and sample or unknown fuel gas of interest are fed to the inlet conduits 63 and 62 and the motor 61 which is preferably a stepping motor is energized through the electronic system which includes a stepping motor drive control (discussed in detail below in conjunction with the discussion with the electronic system).

As the shaft of the stepping motor rotates, the direct coupled rotor 100 of the air-fuel proportioning system also rotates at the same speed. The air groove 118 in the distribution member 101 is continuously supplied with air, the groove 119 is continuously supplied with sample. Rotation of the member 100 together with the aligned seals 111 and 112 aligns and connects each of the cylindrical passages 122 alternately with the groove 119 and the groove 118.

The members 101 and 102 are disposed in fixed alignment such that the corresponding air grooves 118 and 120, and the fuel grooves 119 and 121 face each other through the rotor 100. Thus, any given port 122 aligned with the supply groove 118, of course, connects to the outlet groove 120 such that during this time, the contents of any aligned cylinder are caused to flow into the outlet groove 120 and through the port 129, and the corresponding hole 122 is filled with air. Upon reaching the position of the aligned grooves 119 and 121, the port is then exposed to the sample fuel, and the air is expelled or pushed out through the port 130 and the cylinder 122 filled with the sample fuel such that when the angular displacement of the particular cylinder 122 again aligns with the grooves 118 and 120, the fuel will be displaced by air with the fuel being dispensed through the port 129.

As can be seen in FIG. 5 the annular air grooves 118 and 120 are much longer than fuel grooves 119 and 121. Nominally the air grooves may encompass about 240° and the fuel grooves 60° with two 30° spaces therebetween. This allows for the continual passage of an amount of air through the system. It can also be readily seen that the ratio of fuel to air reaching the groove 120 and passing through the outlet port 129 and eventually the burner 45 (FIG. 2) will be directly proportional to the angular speed of the rotor 100. The faster that the rotor rotates, the higher the proportion of fuel to air that will be passed into the main combustion system.

So far as the mixture vented through the opening 130 through conduit 65 is concerned, the theory of "plug" flow would dictate that since the fuel which had been picked up by any given cylindrical volume chamber 122 would have been exhausted at the groove 120, only air would be exhausted through the vent at 65. In reality, however, because of some diffusion mixing, the gas is not entirely purged from each of the cylindrical volumes 122 of the rotor 100 such that a minute amount of residual fuel is expelled in the mixture at outlet opening 130. This adds to the overflow of the supply gas which is sufficient to sustain the small vent burner or flare 53. If necessary an auxiliary supply line (not shown) may be provided from the sampling system inlet line 62 in a well known manner to sustain the flame in the burner 53.

The inlet and outlet ports connecting the grooves are preferably located at the extremes of the grooves in either embodiment. In the case of the fuel system, the inlet of the shorter groove should be at the point last encountered by the rotor and the effluent exit should be at the end of the groove or slot first encountered. In this manner, the fuel tends to flow through the supply slot and the effluent through the exit slot in a direction opposite to the direction of rotation of the rotor member. The inlet and outlet accesses for the air and mixture of interest, the inlet should be at the extreme first encountered by the rotor and the mixture outlet at the extreme last encountered by the rotor such that the air tends to flow in the same direction as the direction of rotor rotation. This enhances the operation of the system to achieve improved purging and mixing.

The important point is the fact that equilibrium is soon reached and precise repeatable desired ratios of fuel to air can be obtained through the outlet opening 129 such that the mixture at the main burner 45 may be precisely controlled in accordance with the speed of the rotor 100. This, in fact, is accomplished with a great degree of accuracy. The air, of course, continually flows through the system as there are always cylindrical volumes 122 connected between the air supply and the outlet to the main burner 45 through the rotor 100.

Figure 6:
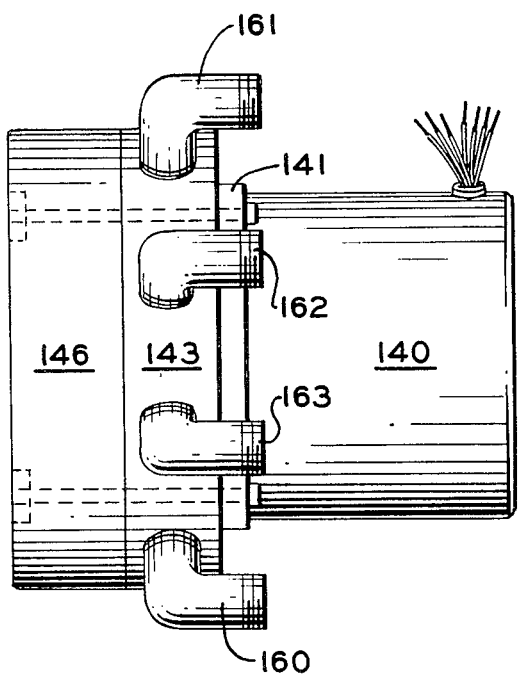
FIG. 6 is an enlarged view of an alternate rotary valving system of the embodiment of FIG. 2.
Figure 7:
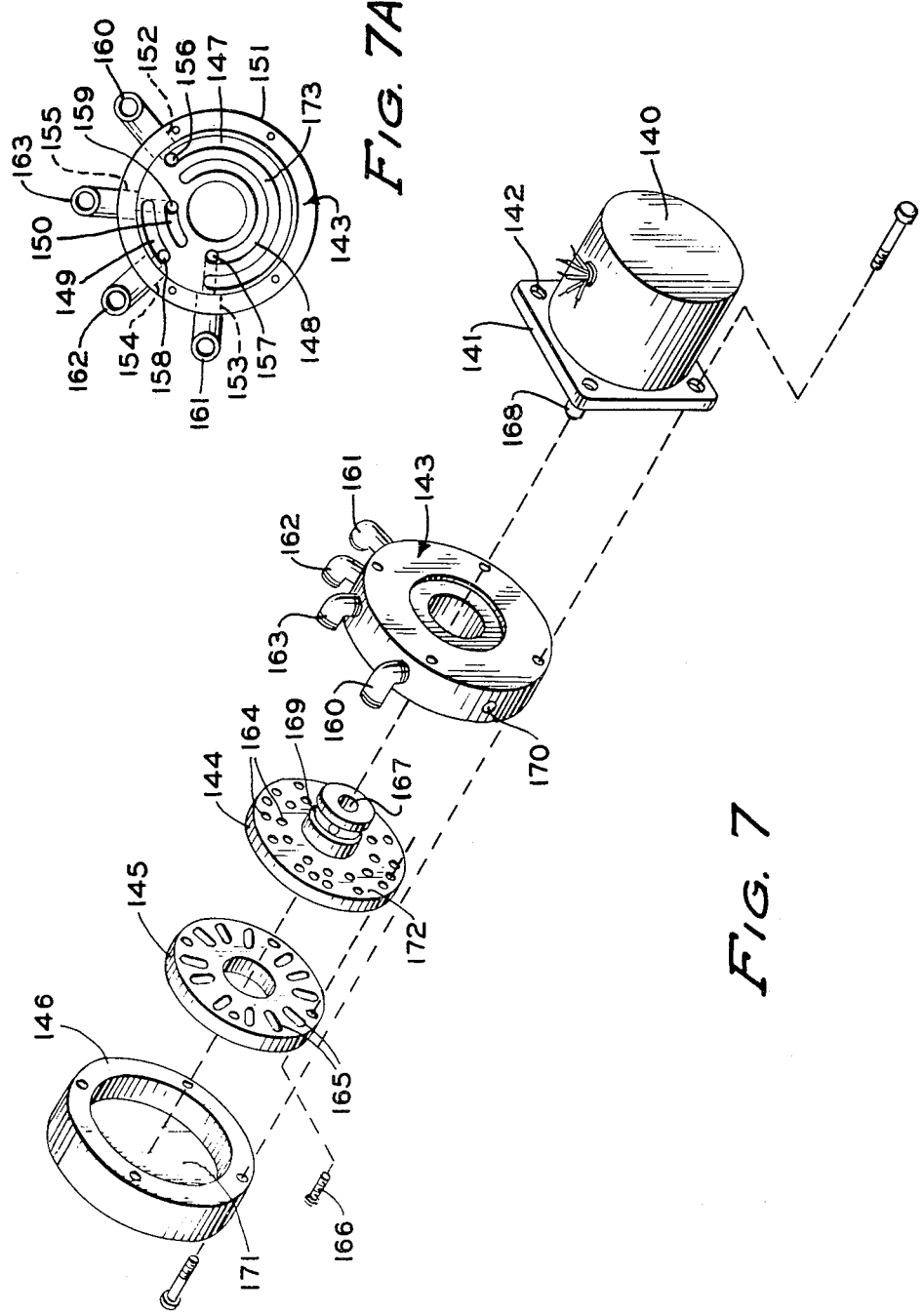
FIG. 7 is an exploded view of the rotary valving system of FIG. 6.

An alternate embodiment of the rotary air-fuel proportioning system 60 is shown in FIGS. 6 and 7. This embodiment may be interchanged with the previously described embodiment 60 in fuel heat content measuring system of FIG. 2.

In FIG. 6 there is shown an elevational view of the alternate embodiment of the rotary valve, the exploded details of which are shown in FIG. 7. This system includes a motor 140 similar to 61 which may have an integral base 141 with mounting holes 142, air-fuel distribution stator member 143, a rotor member 144 with associated plate 145, and a cover member 146. The stator distribution member 143 is provided with annular disposed recessed grooves or slots. These include longer slots 147 and 148 and shorter slots 149 and 150 which may be recessed in the surface in a shape rectangular or semicircular in nature as with the slots of the embodiment previously described. Four access ports are provided from the circumference 151 of the stator distribution member 143 at 152–155 which may be in the form of radially disposed drilled holes which are located below the bottom of the grooves 147–150 and connected to the respective grooves as by four holes in the base of the grooves as at 156–159. The access ports 152–155 are then respectively connected as by four inlet elbow pipe fittings 160–163 as shown in FIG. 7. In this fashion, inlet fitting 160 is directly connected with to the groove 147, outlet fitting 161 to groove 148, inlet fitting 162 to groove 149, and outlet fitting 163 to the groove 150.

The rotor member 144 is provided with two concentric, symmetrically distributed series of radially disposed holes 164 aligned radially in pairs. The member 145 is provided with a series of radially disposed recesses in the form of grooves or slots 165 such that when the relative positions of the rotor 144 and member 145 are in proper alignment, each of the radial pairs of holes 164 aligns with a recessed slot 165 therewith forming a "U" tube of defined volume. The members 144 and 145 are secured together as by screws or bolts at 166.

When assembled, the hollow shaft 167 of the rotor member 144 is keyed to and receives the motor shaft 168 and is secured thereto as by set screws at 169. Access to the set screws may be provided as by an additional radial opening 170 beneath the grooves in the face of the stator distribution member 143. The unitary structure including members 144 and 145 is adapted to be received in the recess 171 of the cover member 146 such that it is free to rotate therein. However, the smallest practical clearance should be maintained between the rotating structure front face 172 and the front face 173 of the stator member 143. This assembly is bolted together as through holes 142 in motor mount 141 to stator 143, and through holes 174 in cover 146 to stator 143 to secure the assembly together with the unitary structure including combined members 144 and 145 free to rotate with the motor shaft within the assembled housing in extremely close proximity to the member 143.

In this manner, a series of radial "U" tubes are provided connecting the inner and outer grooves of the stator 143. The fittings 162 and 163 are connected to fuel in and fuel out or vent lines corresponding to lines 62 and 65 of FIG. 2. Fittings 160 and 161 are respectively connected to incoming air and precisely-ratioed mixture lines as at 63 and 64 of FIG. 2.

One successful embodiment utilized 12 U-tubes symmetrically radially distributed in the combined rotor member which yields a 30° separation. The shorter slots 149 and 150 in the stator member 149 subtended an angle of 60° and the longer grooves or slot members 147 and 148 subtended an angle of about 240° of the circumference of the member 143 with 30° separating both extremes of the grooves. This, of course, means that at least two of the "U" tube members will always be aligned connecting the slots 149 and 150 and at least eight "U" tube members likewise will always connect the corresponding slots 147 and 148 at any given instant in time no matter what the relative rotation position of the combined member 144-145.

The operation of the proportioning system of this embodiment is easily described by selecting any "U" tube system and following its progression as it rotates about in the system. At some point in time, a given "U" tube will encounter the fuel section of the system connecting slots 149 and 150 such that regulated volumetric flow of fuel flows through the opening 158 filling and purging the slot 149 and the given "U" tube, also purging and filling the slot 150 and finally leaving through opening 159 and fitting 163 into the vent or flare gas line to be vented and burned at 49 in FIG. 2. The fuel flow rate, highest anticipated motor speed, and "U" tube volumes are sized such that for any reasonably anticipated stoichiometric air-fuel ratio, the "U" tube will be completely filled with fuel and all the air expelled during the interval in which it connects the slots 149 and 150. Continued rotation brings the "U" tube across a 30° blank section of the stator and the metered fuel in the "U" tube remains trapped therein. As the fuel filled "U" tube is exposed to the 240° segment of the slots 147 and 148, air is allowed to enter at the controlled volumetric flow rate and proceeds through the system. During this interval the U-tube connects slots 147 and 148 such that air entering the pipe fitting 160 pushes the fuel contained in the "U" tube into slot 148 and eventually out through the radial hole 153 and fitting 161. The fuel, now mixed with air, proceeds as through line 64 in FIG. 2 to the sample or main combustion burner 45 where it is burned in accordance with the present invention.

From the configuration, it can be seen that eight "U" tubes are exposed to air simultaneously and that the mixture in line 64 will be a mixture of the flows from all eight "U" tubes. It can also readily be seen that the air flow supplied to the combustion chamber through the rotary proportioning system is totally independent of the rotary valve operation inasmuch as there are always the same number of U-tubes supplying air. The fuel flow rate, on the other hand, is determined by the frequency at which "U" tubes are filled and flushed by the air, that is, the rotational speed of the valve and the volume of the "U" tube. Of course, the U-tube volume is constant for any particular device. Therefore the air-fuel ratio at the burner 45 will be directly proportional to the speed of the rotary valve within the limits stated above.

In FIG. 3 there is shown an alternate embodiment to that of FIG. 2 which is similar except for the proportioning system. The sample gas inlet system for that embodiment is similar including a supply line 200 which leads successively to a filter 201, pressure regulator 202, and metering orifice 203, and inlet valve 204. Likewise, a calibration gas system may be similarly provided for calibrating equipment including an inlet line 205, filter 206, regulator 207, and orifice 208. The air inlet system includes a supply of air as from blower 209, pressure regulator 210, and metering orifice 211, supplying air to inlet line 212.

The valving system of the air-fuel proportioning system includes three-way valves 213, 214, 215, and 216. These are joined together as shown by cylindrical chambers 217 and 218 and conduit lines 219, 220, and 221. The system is connected to a mixing chamber 222 by conduit 223 and, in turn, the mixture is introduced to combustion chamber 224 by conduit 225. Further lines 226 and 227 lead to a vent or flaring combustion chamber 228. The measuring or main combustion chamber contains a burner 229 and a electrochemical sensor 230 along with an igniter flame safeguard device 231 with associated flame sensor-igniter 232. Likewise, the vent or flare combustion system at 228 also contains a burner 233, associated safeguard device 234, and associated sensor-igniter 235.

In normal operation the gas of interest enters as through the conduit member 200 which may be permanently attached to a fuel line, or have other means for temporary connection to a source of sample fuel gas, the heat content of which is to be measured. As with the preferred embodiment, the gas passes through the filter 201 and the pressure and flow rate are regulated by regulator 202 with orifice 203 adjusted to give the desired flow rate. When used, the calibration gas enters the system in the same fashion at 205. The three-way valve 204 is normally in the position such that the fuel gas of interest will enter the system through ports A and C. Port B is shut off thus isolating the calibrating gas. During calibration of the instrument, the valve is switched either manually or automatically to allow calibration gas to enter through ports B and C with port A shut off thus isolating the sample gas. Likewise, air provided by the blower 209 is regulated in flow and pressure by the regulator 210 with orifice 211 and enters the system through line 212.

The proportioning system of this embodiment of the invention is provided by the combination of four three-way valves 213–216 in conjunction with cylinder sections 217 and 218 which are of a precisely known volume. The three ports of each valve have been designated by the letters A, B, or C. If we envision each of the valves as being in one of two possible positions, we can designate the system position I to be one in which all ports designated A are connected with all ports designated C and all parts B are closed. With the system in position I, then, fuel in conduit 219 is directed through valve 213 into and filling the cylinder 217, through valve 214 into line 227 and vented through the venting burner system at 228. Simultaneously, air proceeds from line 220 through valve 215 filling cylinder 218 and is exhausted through valve 216 and lines 221 and 223 into the mixing chamber 222.

When the position of the four valves 213–216 are switched, all ports labeled B and C are then connected. This can be designated position II. With the system in position II, fuel flows from line 219 through valve 215, cylinder 218, valve 216 into the vent gas system, and, conversely, the air flow is through valves 213 and 214 and again into the mixing chamber 222.

It can be seen from FIG. 3 and the above description that in position I, with all ports A and C connected, only the precise amount of gas contained in cylinder 218 between valves 215 and 216 is pushed by air from conduit 220 into the mixing chamber 222. The remainder of the flow is air. Simultaneously, fuel gas is filling the cylinder 217 between valves 213 and 214 with all the excess being vented through the vent burning system at 228. In position II, the precise opposite is true with the air pushing the precise volume filling cylinder member 217 between valves 213 and 214 into the mixing chamber while the cylinder 218 between valves 215 and 216 is refilling with the fuel gas. In either case, all the excess fuel gas is vented through the vent or flare system 228 and all the air, in either position, in goes to the mixing chamber 222. Therefore, as the four valves 213–216 switch alternately between positions I and II, etc., precise amounts of fuel contained in the cylinder sections 217 and 218 between the respective valves are alternately pushed into the mixing chamber by the air supply.

The air and fuel mixes in the chamber 222 and proceeds through conduit 225 into the measuring or main combustion chamber 224 where it is combusted by the burner 229 and the products of combustion are sensed by the electrochemical cell sensor 230. As will be described in greater detail below, the signal from the electrochemical sensor on line 240 proceeds to the signal processing electronics.

The air-fuel ratio eminating from the mixing chamber 222 to the burner 229 may be precisely varied simply by modulating the switching frequency of the four valves 213–216. This is accomplished in a well known manner through a multiplexing system with associated electronic signal processing means. Thus, as the frequency of the valve switching increases more volumes of gas of interest from the cylinder sections 217 and 218 are caused to enter the mixing chamber during any unit amount of time. Because the mixture supply is constant, this enriches the mixture. Conversely, if the frequency is decreased, the mixture becomes more lean. The only limitation, of course, is the switching ability of the valves and the corresponding volumes of the cylinder members. If the volumes of the cylinders 217 and 218 are kept small, the frequency which the system can be switched is limited only by the response time of the valves 213–216. It is also desirable to keep the mixing chamber 222 small so that the gas being burned at the burner 229 takes less time to reach an equilibrium mixture at a given switching rate.

It should be noted that provision may be made to compensate for differences in the inlet temperature and fuel gas of interest. A temperature sensor $T_1$ with corresponding signal conductor 241 may be provided to sense the temperature of the air admitted to the system and a second sensor T₂ with lead 242 to measure the mixture temperature. The signals on 241 and 242 can then be used to apply any required volumetric correction to the fuel proportion in accordance with the gas laws in a well known manner as described below in relation to the preferred embodiment.

In accordance with the embodiment of FIG. 3, the valves 213-216 may be any high duty cycle, electrically switched valves such as poppet valves. Valves which have been successfully used include Model S4P18C2B manufactured by Valcor Engineering Corp. of Kenworth, New Jersey, which have an approximate switching time of S-86.

In accordance with either the embodiment of FIG. 2 or FIG. 3, the pre-mix burner which does not require secondary or atmospheric air to operate properly and which will function at the desired flow rate.

The vent gas burners may be any conventional atmospheric burner such as a Bunson burner. It has been found that during the operation of the system the burner flame will be sustained by the vented effluent gases. However, provision may be made for auxiliary fuel and air to be supplied from the system if desired. The flame sensors and flame safeguard units are highly conventional and readily available commercially as a model S-86 manufactured by a assignee of the present invention. In either embodiment, the pressure regulators may be any accurate low flow, low pressure regulators such as 912 series pressure regulators available from the Fisher Controls Company of Marshalltown, Iowa. The main burner of either embodiment is typically operated at a pressure of about 0.5 in. w.c. and a firing rate of about 6.0 c.f.h. of mixture.

As can be seen from the above, the valving system depicted in FIG. 3 along with the rotary proportioning systems of FIGS. 4-5 and 6-7 provide accurate, predictable means for combining two fluids in any desired proportion. The proportion can be determined simply from the rotational speed of either alternative embodiment of the rotary valve or by the switching speed of the valving system of FIG. 3.

Of course, the embodiment of FIG. 3 also has interface with the electronics of the system in a similar manner as the embodiment of FIG. 2. Likewise, sensor 230 is provided with an electrical lead 240 and flame safeguard units 231 and 234 provided with leads 243 and 244, respectively.

As is well known in the art, the open-circuit voltage of a simple electrochemical cell is established by a chemical potential difference which may be based on composition, concentration, pressure, etc., between the anode and the cathode compartments. The particular species to which the cell is sensitive is the same for both the anode and the cathode compartment, the open-circuit voltage should be zero. If, however, one of the electrode compartments is exposed to a reference quantity of the specie of interest and the other electrode exposed to a medium containing a different amount of such specie, an open circuit potential difference is thereby established. Various ceramic compounds are known to establish such electrochemical cells in the presence of differing amounts of oxygen. In the preferred embodiment of the present invention, a modified compound consisting essentially of zirconium oxide ($ZrO_2$) is utilized as a ceramic-based electrochemical cell for the sensor. The electromotive force of the cell is created by exposing one of the electrodes to a medium containing a reference amount of oxygen, namely air, and the other to the products of combustion of the sample fuel of interest in the sample combustion chamber. Thus, when the oxygen concentration in the combustion chamber differs from that of the reference air, a potential difference is set up across the cell which can be measured and/or utilized in accordance with the present invention.

The $ZrO_2$ sensors of the present invention are normally stabilized with CaO, MgO, or $Y_2O_3$ which enhances the chemical and physical stability of the zirconium oxide for use as a sensor. The typical configuration of an electrochemical sensing cell in accordance with the present invention may be represented by

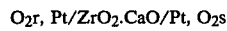

$O_{2r}$, Pt/$ZrO_2$.CaO/Pt, $O_{2s}$ where r stands for reference and s sensed or sample. Noble metal, normally platinum, electrodes are utilized in conjunction with the anode and cathode of the zirconium oxide sensor.

Figure 18:
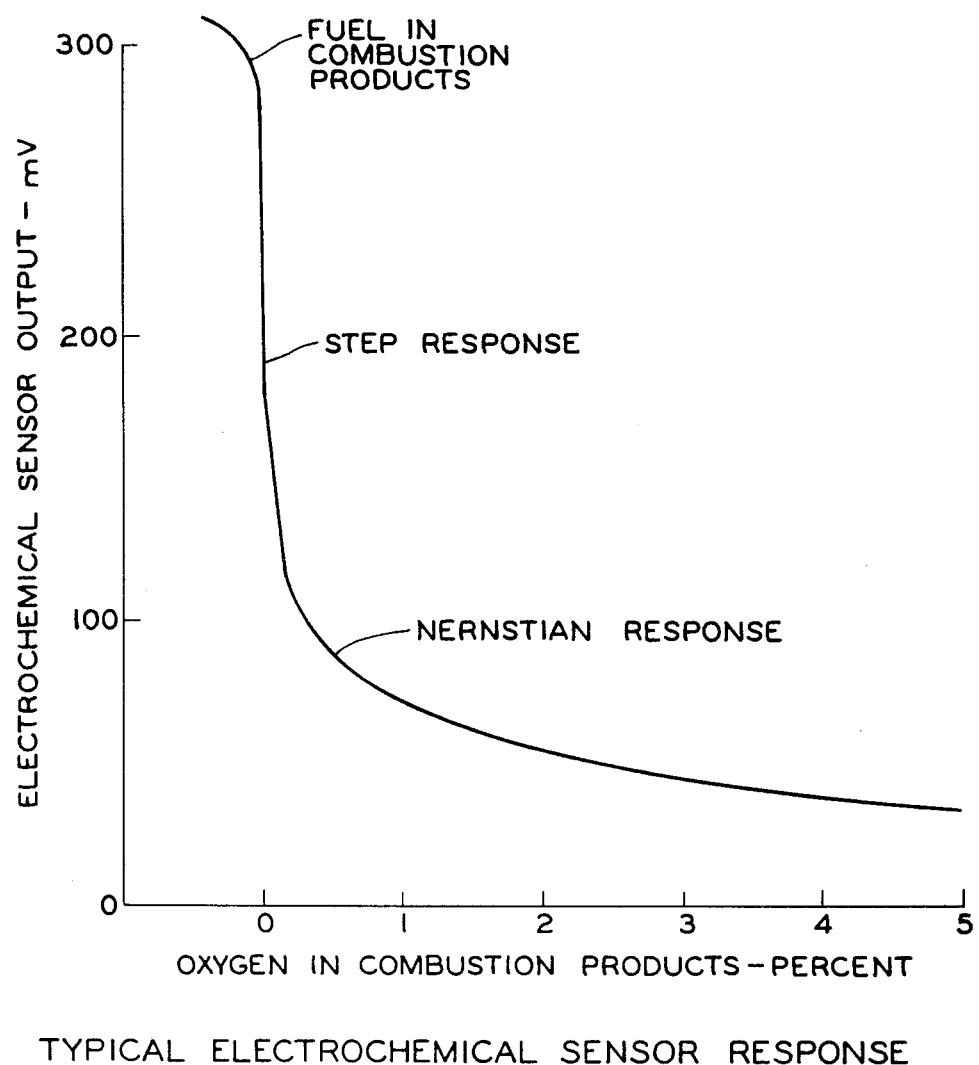
FIG. 18 is a representative curve of the response in millivolts versus the air fuel ratio of a typical $ZrO_2$ sensor in accordance with the invention.

As can be seen in the curve of FIG. 18, in the rich portion of the curve, which indicates the presence of excess combustibles, and in the lean portion of the curve (representing excess oxygen in the combusted gases), the curve does not change a great deal with respect to change in either the concentration of combustibles or oxygen but the center portion of the curve, however, which is close to the stoichiometric point or the point where the amount of oxygen present is just sufficient to oxidize the hydrocarbon components, the curve undergoes the step change function wherein the voltage output varies a great deal with very little change in oxygen concentration in the combustion chamber.

It has been proposed to use the $ZrO_2$ sensor in the lean portion of the curve to relate the partial pressure of oxygen present to the air-fuel ratio. As previously stated, as the amount of excess air increases above the stoichiometric point, a non-linear curve results. This portion of the curve has been found to be a Nernstian response region wherein the variation of the cell open-circuit voltage with the partial pressure of oxygen present at the measuring electrode is given by the well known equation:

$$E = (RT/nF) \ln (P_{O_2 ref}/P_{O_2 sens.}),$$

wherein E is given in voltage units (volts) R and F are constants and T equals the absolute temperature. It can readily be seen from this equation that the voltage output varies inversely with the natural logarithm of the partial pressure of oxygen in the combustion chamber and directly with the absolute temperature. Making use of data desired in this region of the curve, of course, requires very accurate temperature and voltage measurements in order discern the applicable air-fuel ratio. Otherwise errors are easily introduced in the results.

Unlike prior art systems which suggest measuring the residual oxygen in the Nernstian response region, the present invention contemplates utilizing the step response evident at or near the stoichiometric point in which the output of the cell varies greatly with an extremely small change in the air-fuel ratio. This rapid change is far easier to detect and more accurate utilize than are points in the Nernstian region.

Figure 16:
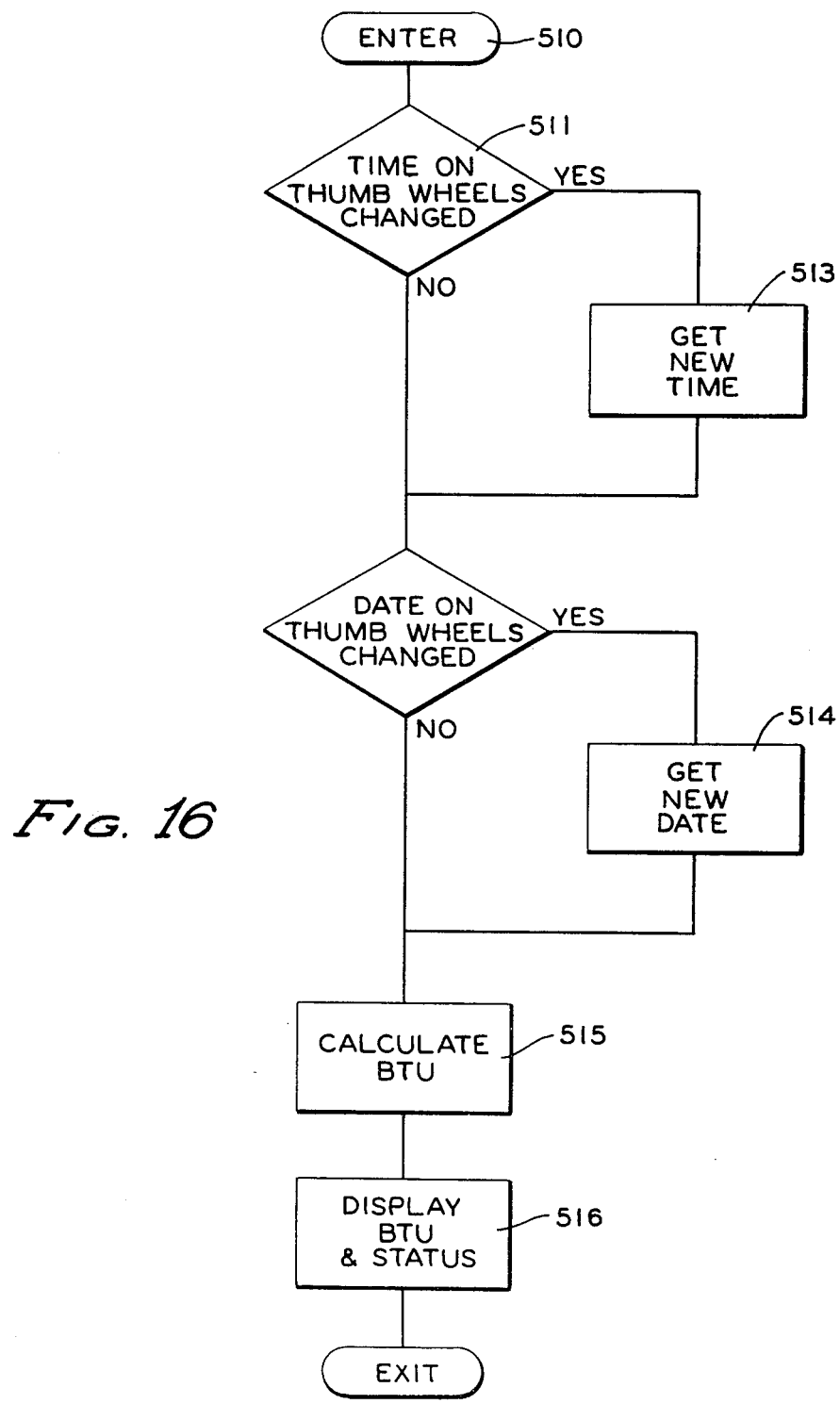
FIG. 16 is a logic diagram of the display task of FIG. 11.
Figure 17:
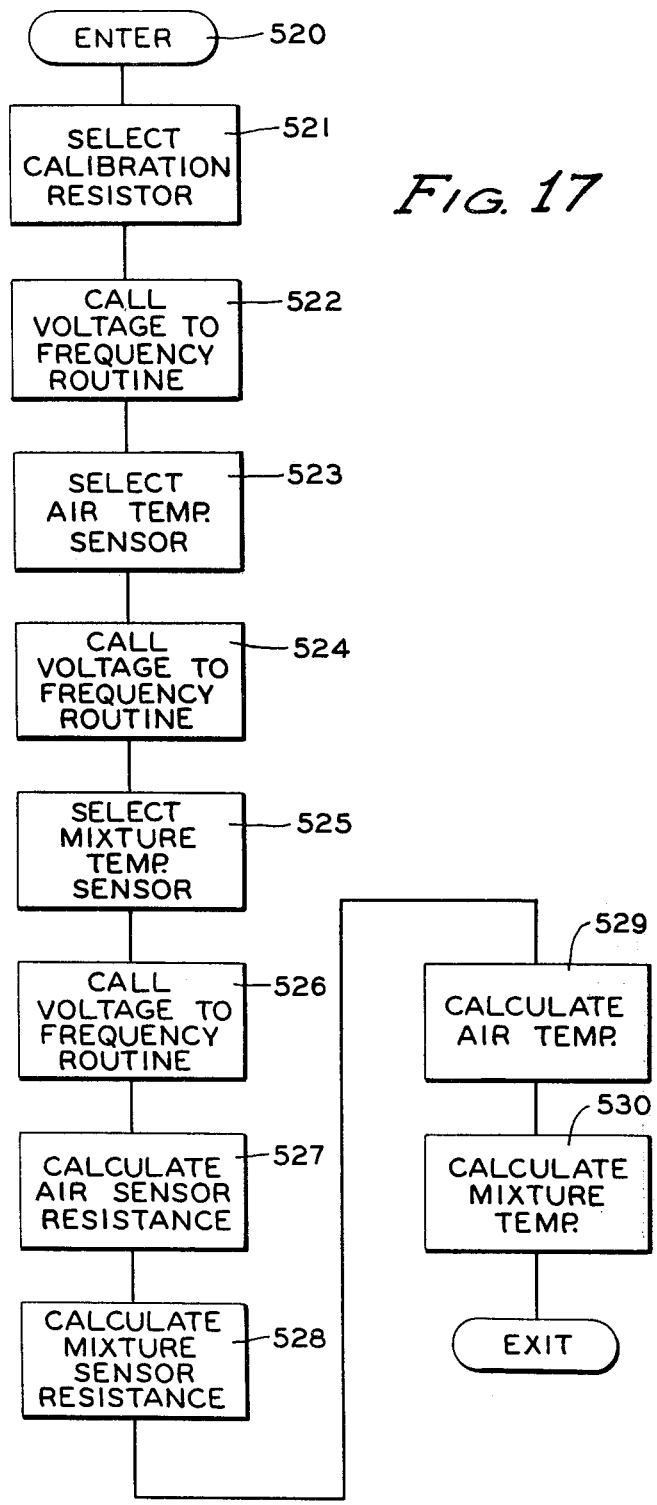
FIG. 17 is a logic diagram of the read temperature task of FIG. 11.

In either embodiment, when the mixture of sample fuel and air is combusted in the combustion chamber, the chemical composition of the combusted gas mixture is sensed by the modified zirconium oxide sensor thereby producing an electrical response in accordance with the curve depicted in FIG. 16. When the mixture in the combustion chamber is such that the products and combustion approach stoichiometry either from the rich or the lean side, an extreme step change is noticed in the output voltage. This step change can be utilized as a control signal of stoichiometry which is repeatably precise and eliminates the errors associated with gradual changes in a curve.

The use of stoichiometric point in the combustion of in the given alkane hydrocarbon fuel gas will now be more fully developed. The stoichiometric combustion equation for methane, the chief component of natural gas fuels, is given by the following equation which assumes that the air utilized for combustion comprises 20.83 percent $O_2$ and 79.17 percent $N_2$ and other inerts:

$$CH_4 + 2(O_2 + 3.76N_2) \rightarrow CO_2 + 2H_2O + 7.52N_2$$

Therefore, wherein $$A/F_{CH_4}$$

represents the air-fuel ratio of methane $$A/F_{CH_4} = (2)(4.76)/1 = 9.52$$

Table 1 represents stoichiometric air-fuel ratios of various alkane hydrocarbons through pentane and adds a column HHV which represents the higher or gross heating value of each particular specie in units of BTUs per cubic foot at 68° F., 14.7 PSIA which are derived MARKS Mechanical Engineering Handbook Seventh Edition. The HHV includes the latest heat of vaporization for steam formed in the combustion reaction. It should be noted that in deriving the actual air-fuel ratios, a value of 0 has been assigned to inerts which normally carry through the system unchanged and an arbitrary value of minus 4.76 has been assigned to each $O_2$ based on its combination with alkane hydrocarbons in the combustion reaction.

TABLE I

| SPECIE | A/F | HHV* |
|---|---|---|
| $CH_4$ | 9.52 | 994.7 |
| $C_2H_6$ | 16.66 | 1742.6 |
| $C_3H_8$ | 23.80 | 2480.1 |
| $C_4H_{10}$ | 30.94 | 3215.6 |
| $C_5H_{12}$ | 38.08 | 3950.2 |
| INERTS | 0 | 0 |
| $O_2$ | −4.76 | 0 |

*$BTU/FT^3$ AT 68 F., 14.7 PSIA (MARKS)

In view of the above, for a sample of mixed saturated alkane hydrocarbons, inerts and oxygen, the air-fuel ratio of a sample ($A/F_s$) may be represented by $$A/F_s = 9.52x_1 + 16.66x_2 + 23.8x_3 + 30.94x_4 + 38.08x_5 - 4.76x_7$$

wherein the x subscript represents the fraction of that hydrocarbon constituent having the given number of carbon atoms through 5 and the 7 has been assigned to oxygen. The higher heating value of the sample ($HHV_s$) then can be given by $$HHV_s = \sum_{i=1}^{5} (HHV_i)(x_i)$$

As explained above, each of the fuel proportioning systems utilized in the heat content measuring system of the present invention depends upon displacing fuel by air from a hollow cylindrical or tubular member at a specific volumetric frequency and running air through the same cylinders for a certain amount of time all at the same controlled flow, that is air. For any of these cylinders, then, the cycle time ($t_c$) can be represented by $$t_c = t_a + t_f \qquad (I)$$

wherein $t_a$ equals the time devoted to the passage of air and $t_f$ represents the time devoted to the passage of fuel. Thus, the time devoted to fuel, $t_f$, can also be represented by $$t_f = (V_i/q_a) \qquad (II)$$

wherein $V_i$ is the volume of any given cylinder and $q_a$ equals the volume flow rate of air. Inasmuch as all the fuel in the system is pushed through the cylinder at the air flow rate, the air and fuel flow rates of flow must be identical on a time basis. Substituting for in equation (II), we have $$t_c = t_a + (V_i/q_a). \qquad (III)$$

Rearranging equation (III), gives us $$t_a = t_c - (V_i/q_a). \qquad (IV)$$

Because of the identical flow rates as explained above, by definition $$A/F = (t_a/t_f) \qquad (V)$$

and, by substituting for $t_a$ by equation (IV) and for $t_f$ from equation (II), we have $$A/F = \frac{t_c - V_i/q_a}{V_i/q_a} \qquad (VI)$$

which, upon simplifying, yields $$A/F = \frac{t_c q_a}{V_i} - 1 \qquad (VII)$$

Also, as explained in conjunction with the description of the apparatus, above, the volumetric flow rate of air may be any arbitrary fixed rate established in the instrument by pressure regulation, volumes, etc., and the volume of each cylinder utilized in the particular proportioning system similarly acts as a limiting constant. Given this situation, let $$K_1 = (q_a/V_i) \qquad (VIII)$$

If we substitute $k_1$ for $q_a/V$ in equation VII, the result is $$A/F = K_1 t_c - 1 \qquad (IX)$$

Figure 19:
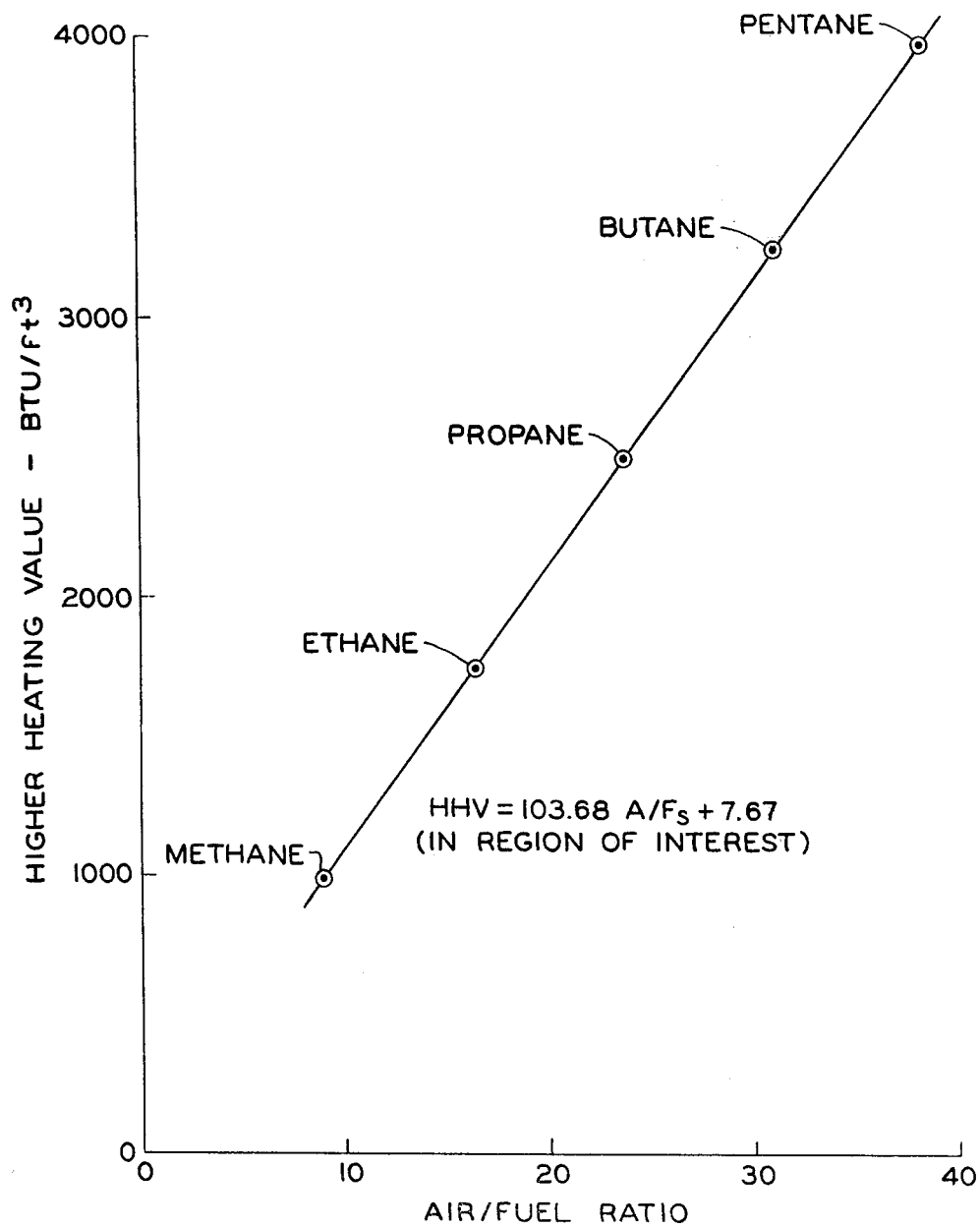
FIG. 19 is a plot showing heat content of various hydrocarbon fuels.

Returning again to FIG. 19, by use of that figure, the following may be derived:

$$HHV_s = 103.68A/F_s + 7.67 \qquad \text{(X)}$$

A combination of equations (IX) and (X) thus yields $$HHV_s = 103.68k_1t_c - 1 + 7.67$$

which upon simplifying yields $$HHV_s = 103.68k_1t_c - 96.01 \qquad \text{(XI)}$$

Inasmuch as the instrument is utilized at a constant mixture flow rate and the volumes of the cylinders for a given instrument remain constant, the constant $k_1$ will be known and thus the $HHV_s$ is rendered directly related to the cycle time of either the or the valving system utilized.

A representative system operating control and measuring electronics implementation is shown in in FIGS. 9 and 10. FIG. 8 shows the sheet layout for FIGS. 9 and 10.

Figure 9A:
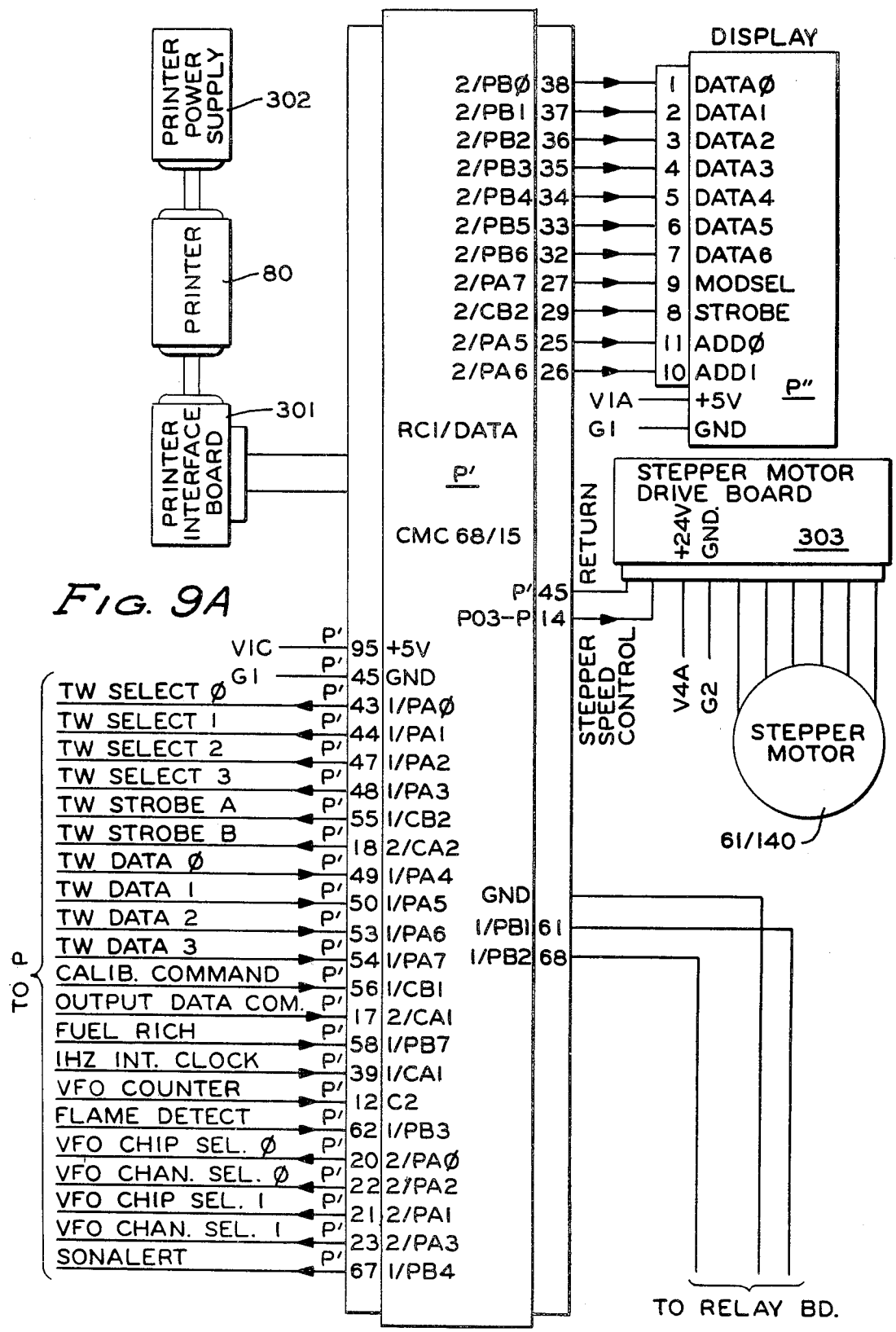
FIG. 9 is an electrical block diagram of the embodiment of FIG. 2.
Figure 9B:
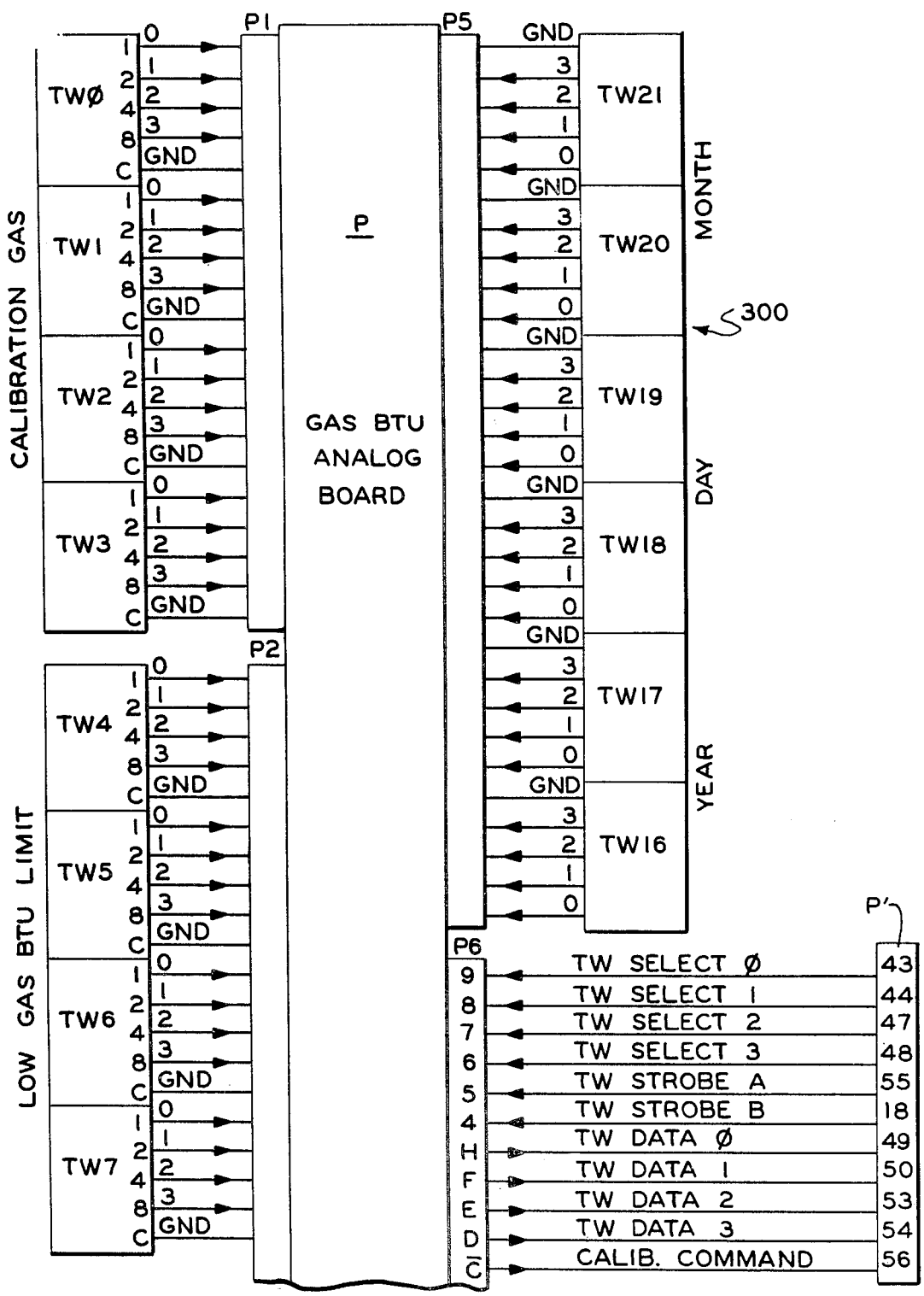
Figure 9B:
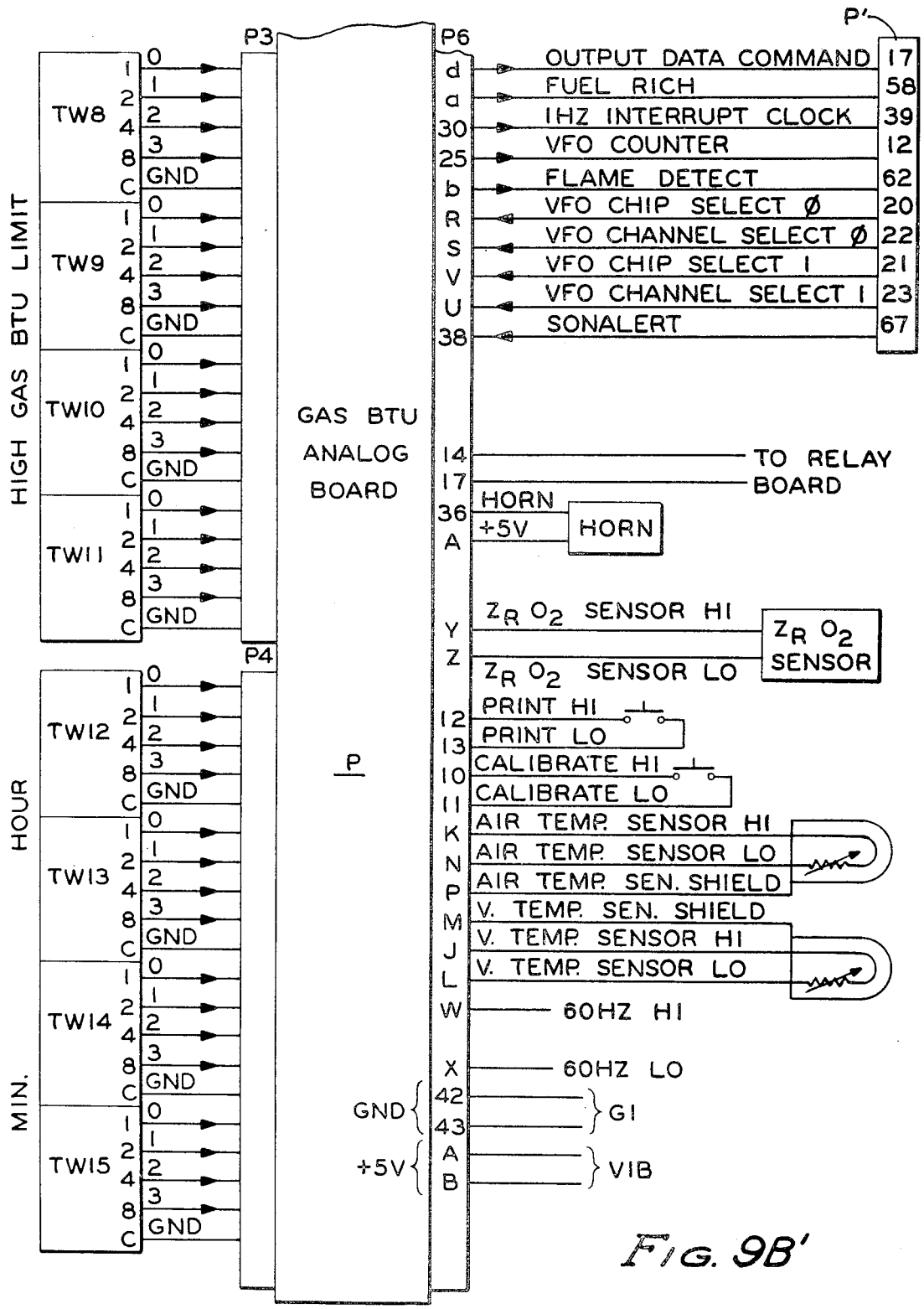
Figure 9C:
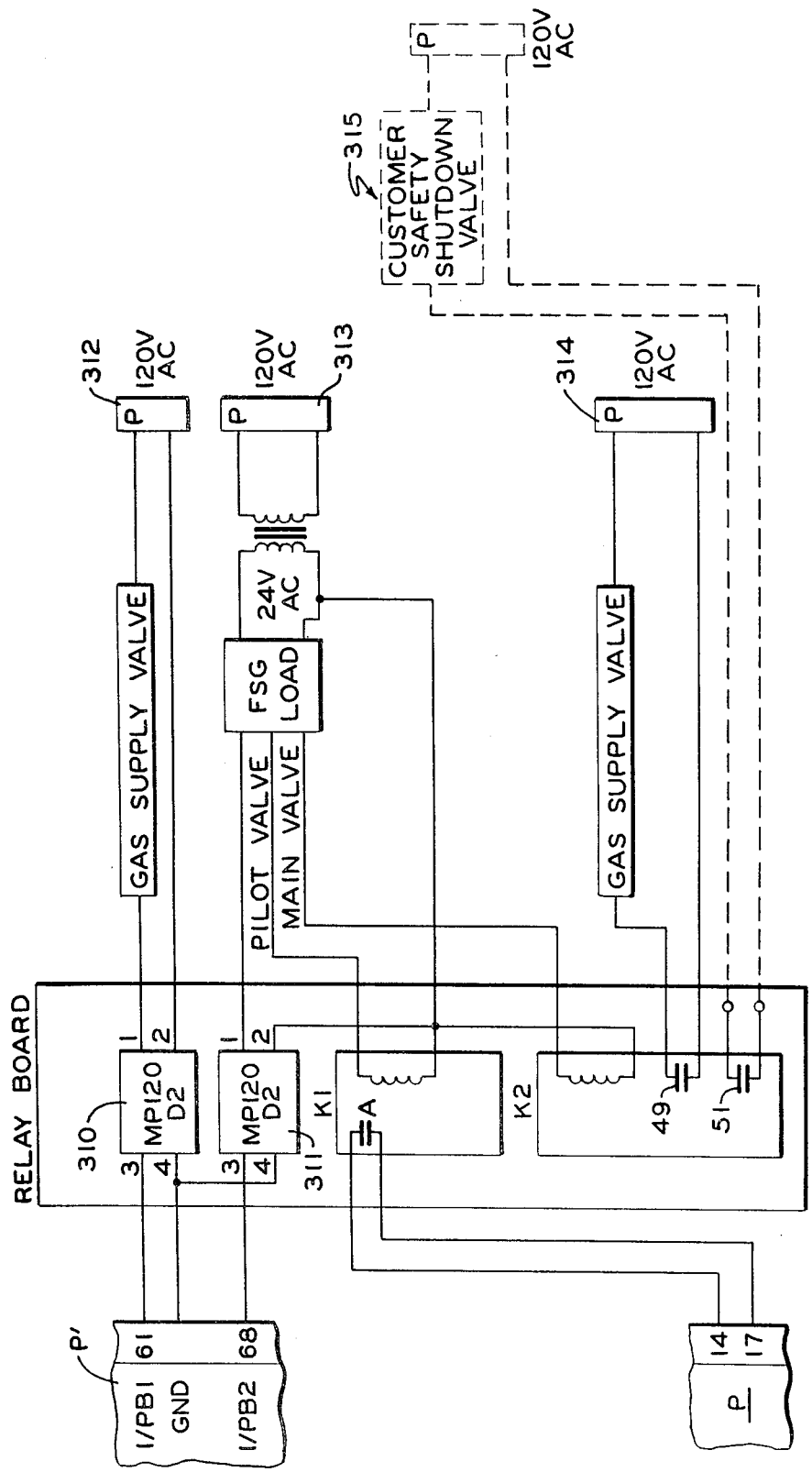

Thus, in FIG. 9A, there is shown an analog board, in FIG. 9B, a microprocessor board, in FIG. 9C, a gas supply and flame safeguard system. Some details of the analog board of FIG. 9A is shown in greater detail in FIG. 10.

In FIG. 9A there is shown the analog board P which includes an array of attached input thumb wheel switches as at 300 and indicates the connections with various other parts of the electronic system including the CMC 68/15 microprocessor control board of FIG. 9B which is designated P'. The numbers and letters designated for the connection to P and P' constitute the pin connections to the board P and P'. A series of pins beginning with P9 and ending with P38 on board P are adapted to line up and connect with pins P'43-P'67 of the CMC 68/15 and the composite of these lines comprise the address and data buses therebetween. Thumb wheel switches associated with the board P are provided to enter data associated with various peripheral functions associated with a particular model of the invention. Thus, such switches are provided to enter data concerning the time, date, BTU, or heating value of a standard or a calibration gas to be used, high and low BTU limit (which are used in association with the metering system described below), etc. The function of the thumb wheel switches 300, including input and outlet are multiplexed in time in a well known manner.

As shown in FIG. 9B, a CMC 68/15 interfaces with the display board P'' which is part of the display system 78 and through interface 301 with a printer 80. A printer power supply is shown at 302. A stepper motor drive board 303 is provided to interface with the CMC 68/15 and to provide the control and modulation for this stepper motor 61 or 140. The CMC 68/15 includes conventional components contained in a conventional, commercially available electronic unit and is available from RCI/Data Corporation of Sattle Brook, N.J. The components include a microprocessor, a memory which includes a random access memory portion (RAM), and an electrically programmed read only memory portion (EPROM), a parallel interface unit, timer, and display unit driver P'''. These units are respectively connected by address buses and data buses in a conventional preassembled board. A serial interface and 1 MHz crystal oscillator clock are also provided.

The components utilized in one CMC 68/15 used in one embodiment were standard off-the-shelf items and they are listed below as follows:
Microprocessor 201: MC6800
Memory 202:
  2114 RAM
  1Kx4
  2716 EPROM
  2Kx8
Parallel Interface 203: MC 6821
Timer 204: MC6840
Display Driver 205: Litronics DL 1650
Serial Interface 214: 2651 Signetics
4 MHz Crystal Oscillator: Knight Individual components available from various manufacturers such as Motorola, Texas Instruments, etc.

FIG. 9C depicts the details of the flame safeguard and gas safety system which may be used with the present invention. In addition to the components described in relation to FIG. 2 include solid state relays 310 and 311 and power supplies 312, 313, and 314. The customer safety shutdown may also be provided as shown by the dashed lines at 315.

In operation, when the system is started, air and gas flow are initiated through the particular system utilized and the burners ignited by the spark ignition in conventional fashion. The flame safeguard units 46 and 54 then indicate the presence of a flame through the signal lines P14 and P17. The signal is debounced as explained below in conjunction with FIG. 10. The debounced signal causes the contacts 49 and 51 to close thus allowing the gas safety valve 56 (and the safety shutdown valve if used) to remain open.

The debouncing circuit is denoted by the dashed line labeled 316. The system basically includes an MC14490 debouncers which stabilizes the relay contacts of the flame safeguard device and also the inputs from the board P' concerning the calibration command and output data command. Also shown on sheet a of FIG. 10 are a threshold detector system indicated at 330 and circuitry associated with the one Hz interrupt clock which controls the program logic sequencing (discussed below) at 330.

The signal from the $ZrO_2$ sensor is compared to a predetermined threshold value in the threshold detector as by a comparator 321. At the point of stoichiometry, the output changes from a low signal to a high signal indicating that the point of stoichiometry has been passed going from air rich to fuel rich. As explained below, when the system is tracking properly, the indication should alternate from air rich to fuel rich, etc., to show that the system is tracking on the point of stoichiometry.

The 1 Hz interrupt clock system 330 includes a counter 331 and a comparator 332. The comparator 332 is utilized to determine when the counter 331 has reached 0 indicating that a full second has passed and it is time to activate the interrupt. The counter is then reset and begins timing for the next sequential interrupt. Counter 331 basically rides a conventional 60 Hz power input down until it equals a 1 Hz time clock.

Figure 10A:
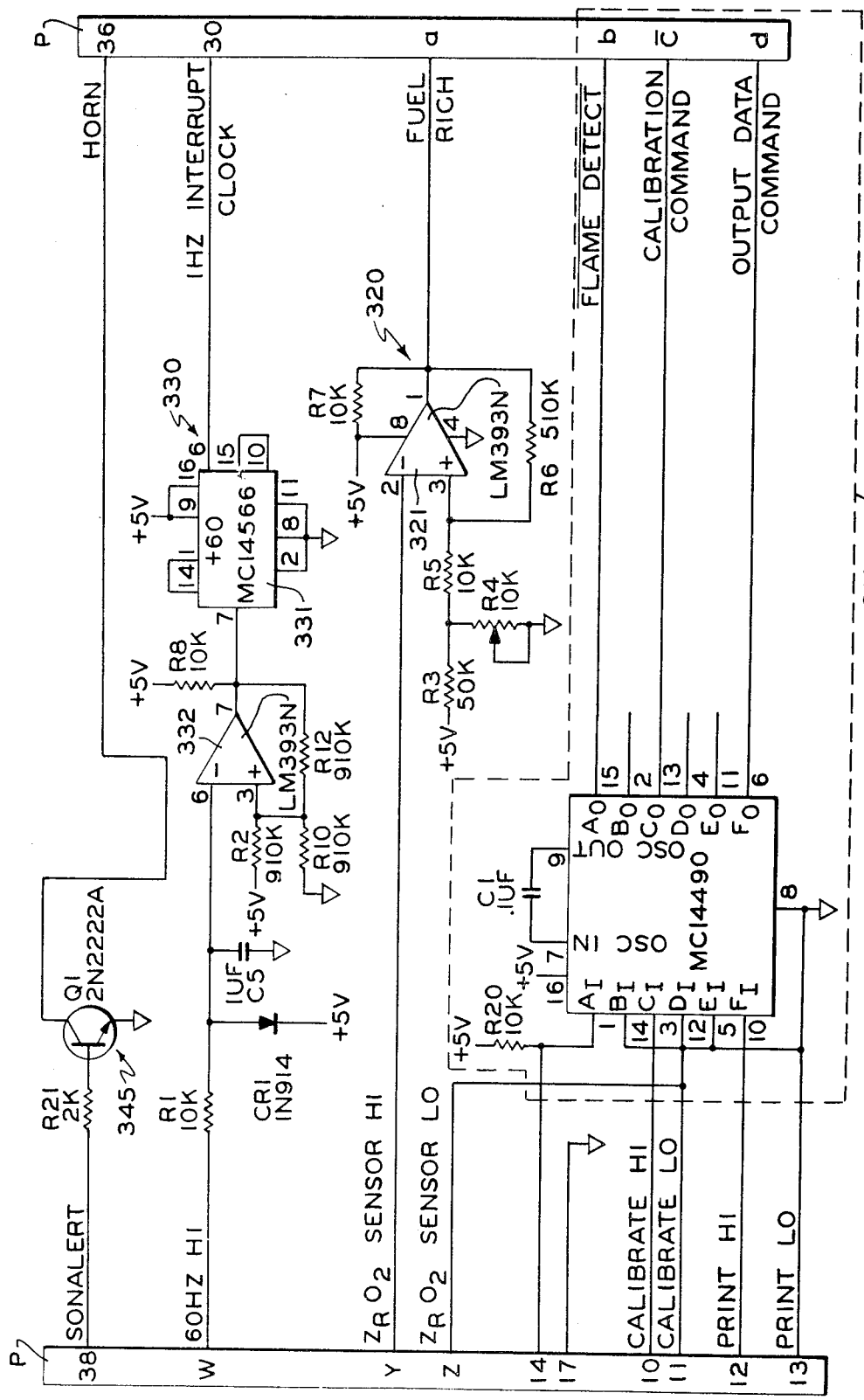
FIGS. 10A and 10B are is a diagram of electrical details of the diagram of FIG. 9.
Figure 10B:
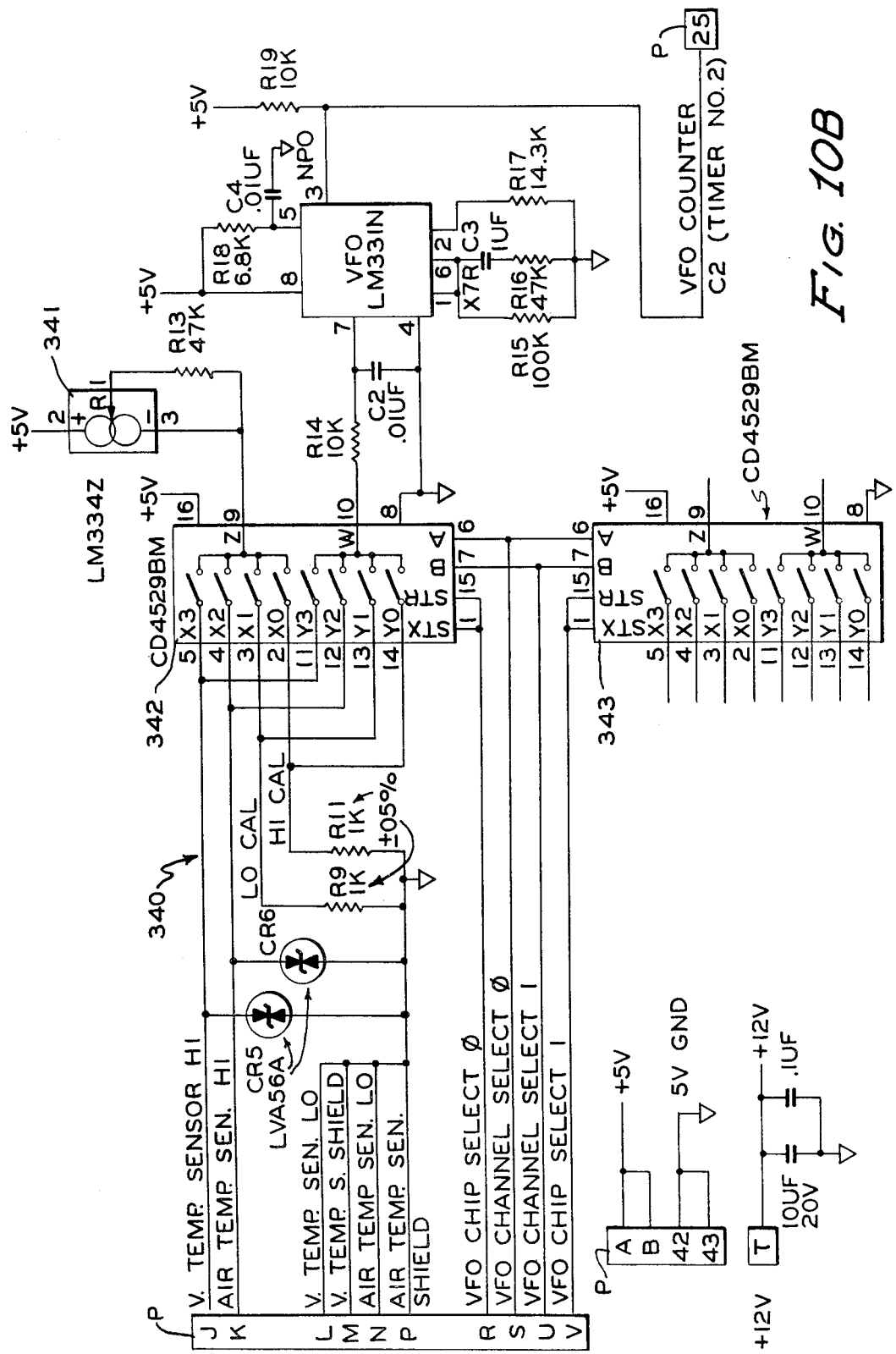

The system indicated by the block 330 in FIG. 10B is basically an analog-to-digital converter system which converts analog data received at various parts of the system into a form usable by the central processing unit of the system. These include high and low temperature limits for the air and gas of the system along with actual values sensed and numbers pertaining to the calibration gas and high and low BTU limit set for the operation of the system as described in greater detail below. The system includes the constant current source at 331, typical analog multiplexes at 322 and 323, and a voltage-to-frequency converter 324 which are combined in a well known manner. The output of the VFO counter is sent to a timer in the CMC 68/15 where the signal is properly multiplexed and the periods measured.

It should also be mentioned in regard to FIG. 10A that the sonalert circuit is shown at 345. The system is designed to sound an alarm when the BTU measurement is out of the limits that have been dialed in on the proper input thumb wheel switches. Circuit 345 provides the driver circuitry for this sonalert.

Figure 11:
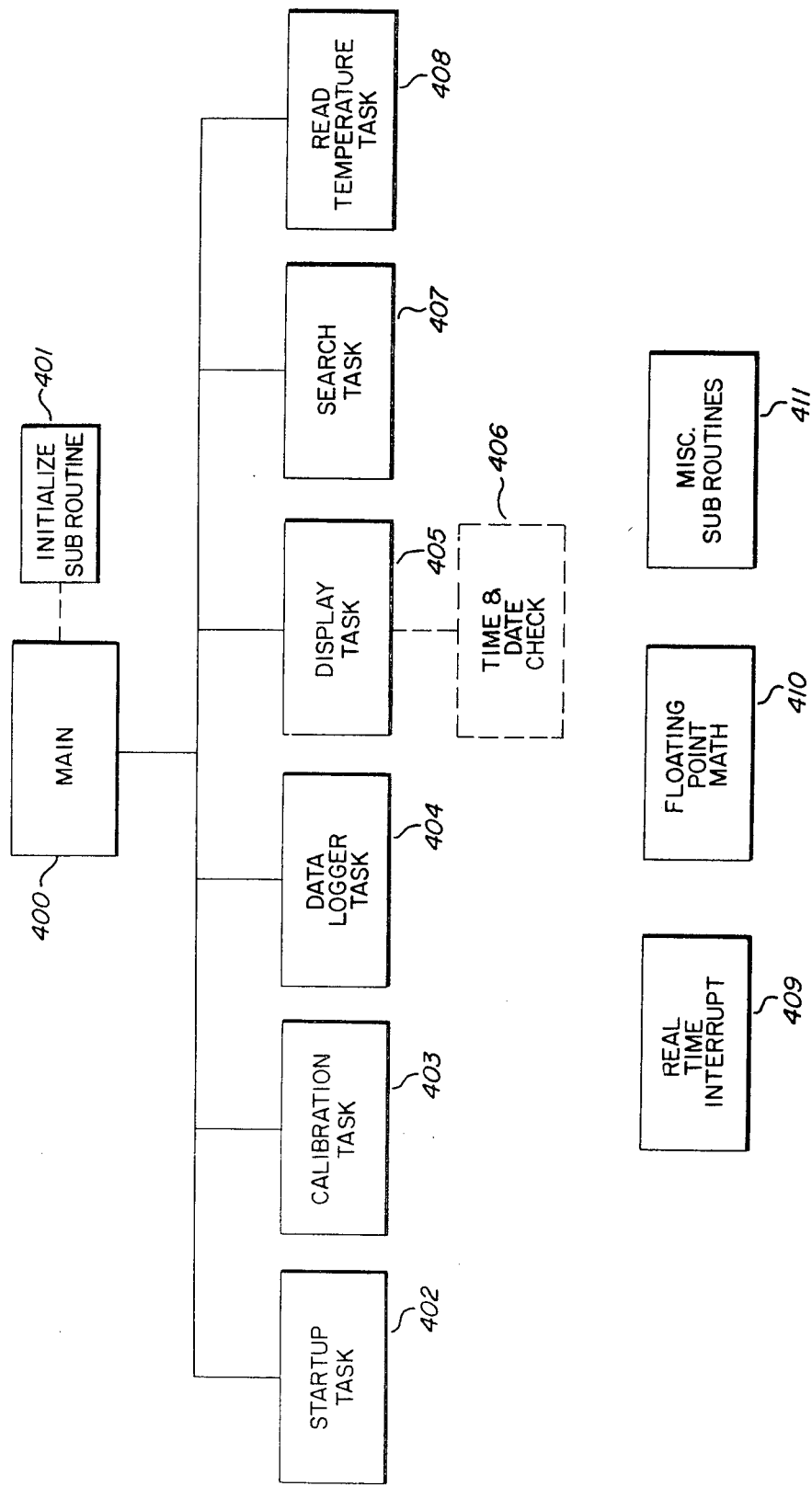
FIG. 11 is a block diagram of the logic diagrams of FIGS. 12-17.

A representative software logic control schematic layout in accordance with the present invention will now be described in accordance with FIGS. 11-17. FIG. 11 depicts a layout of the basic routines shown in greater detail in FIGS. 12-17. They include a main routine 400 with initialize subroutine 401, startup task 402, calibration task 403, data logger task 404, display task 405 with associated time and date check 406, search task 407, display task 407, read temperature task 408. Other associated subroutine are shown at 409, 410 and 411. The main routine, of course, controls the interaction of the various tasks. A particular system described in relation to FIGS. 11-15 involves a system utilizing preferred rotary valve system as depicted in FIG. 2. A complete software listing is included as Appendix A.

Figure 12A:
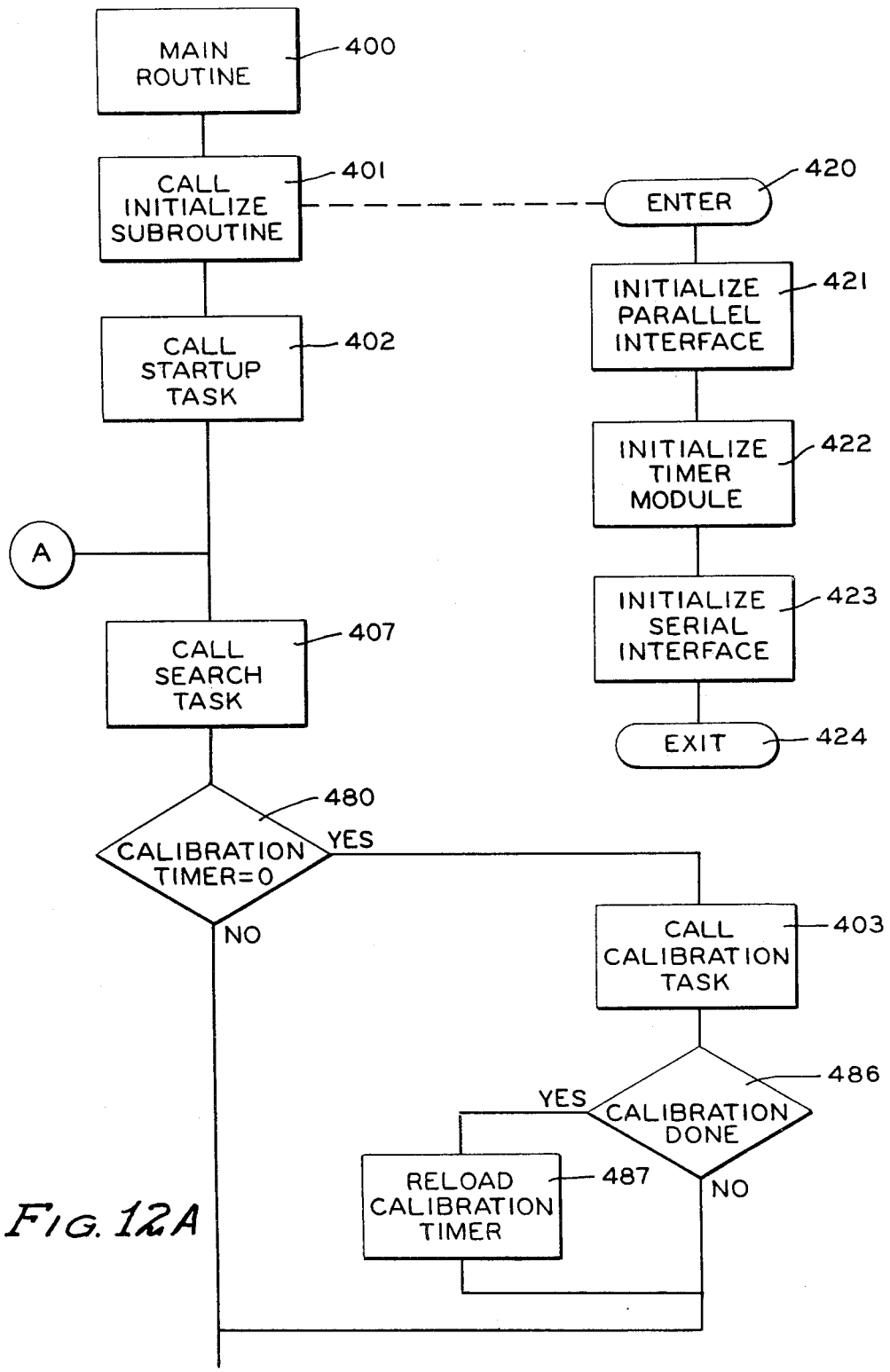
FIG. 12, which includes Parts 12A-12C is a logic diagram for the main routine system of FIG. 11.
Figure 12B:
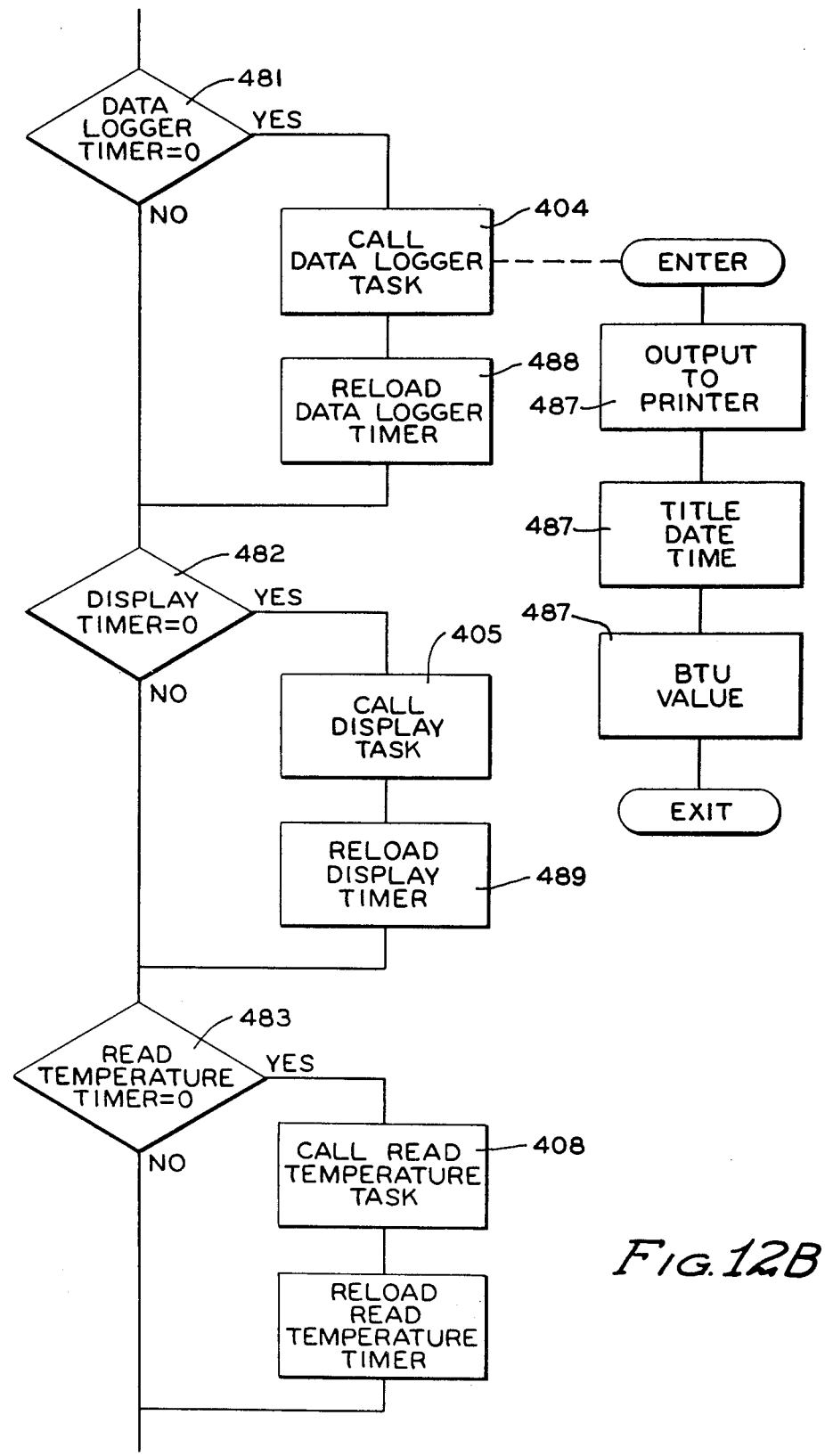
Figure 12C:
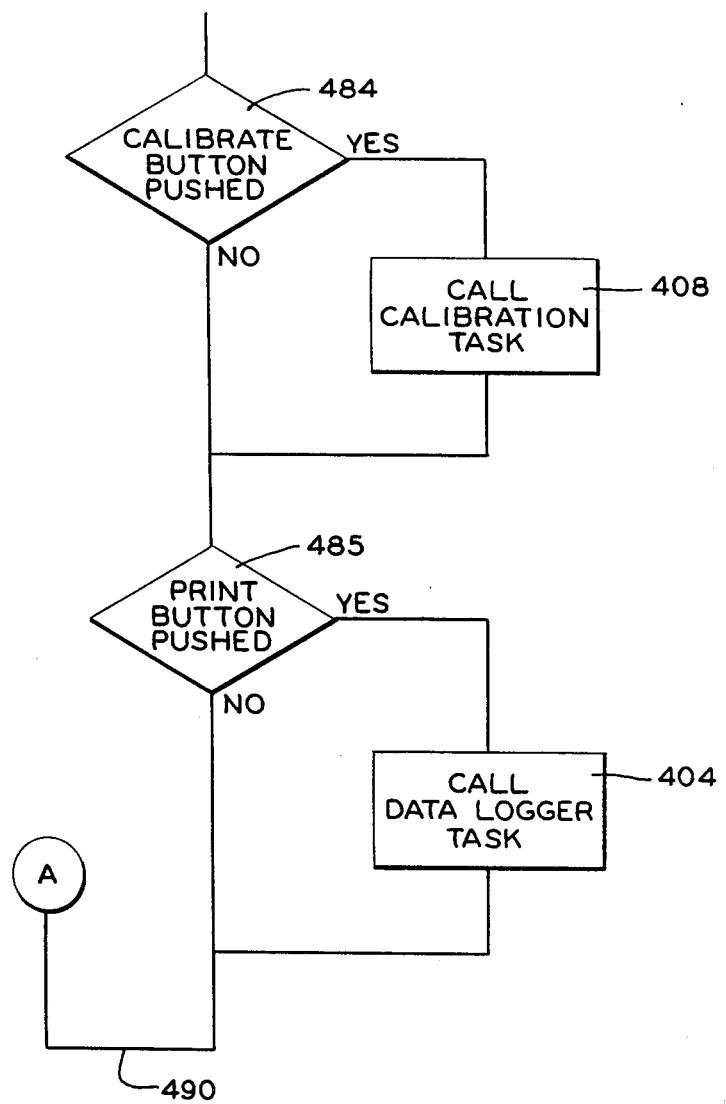
Figure 13:
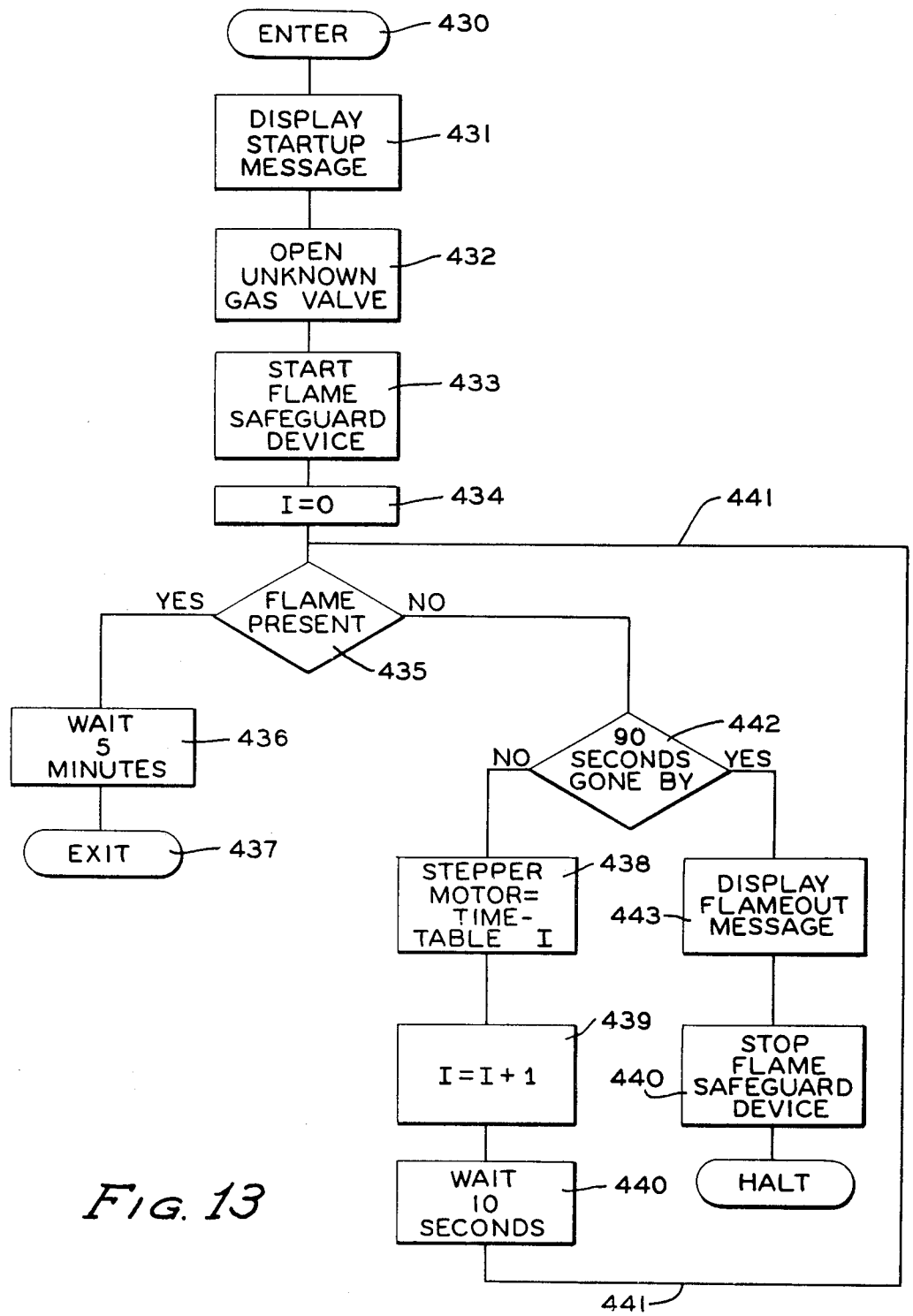
FIG. 13 is a logic diagram for the startup task of FIG. 11.

FIG. 12 depicts the logic diagram for the main routine in accordance with the preferred embodiment. As with all such systems, operation cannot begin until the entire system is activated or initialized as at 401. Upon power of the instrument, then, the first step in the software logic is to call the initialize subroutine which enters at 420 in FIG. 12B. This happens as soon as the instrument is started and before the sampler vent burners are lit. The initialize subroutine then initializes the parallel interface at 421, the time module at 422, and the serial interface unit at 423. These modules are part of the 68/15 board and must be initialized and configured as predetermined in the system. Following this, the initialize subroutine exits at 424 and the main subroutine continues by transferring control from the initialize subroutine to the startup task 402. The startup task is found in FIG. 13.

The logic flow enters at 430 and causes a startup message to be displayed on the display at 431 which tells observers the state of the instrument. The software then initializes the flame safeguard and sparking device to light the gas mixtures at both burners. During startup, the stepper motor is modulated by the frequency of the output of the timer model 422 which was initialized during the initialize subroutine. At startup, the frequency is varied to locate a mixture of air and fuel that will sustain a flame by increasing the values of frequency in accord with a lookup table in the microprocessor EPROM memory. Thus, after the gas valves allowed to be open as at 432 and the flame safeguard device started as at 433, the index 434 is initially at 0 or the first selected frequency in the table. If the flame safeguard system indicates the presence of a flame at 435, a five-minute delay is initiated at 436 to allow the sample gas burner to stabilize and the ceramic sensor to achieve its proper operating equilibrium temperature. At that point, the logic flow exists at 437.

If, on the other hand, presence of a flame is not indicated at 435, the stepper motor frequency is indexed to the next position at 438 and 439 such that the mixture is slightly enriched. A ten-second delay is implemented at 440 so that the mixture may stabilize at the burner. After this delay, the logic flow again is routed to 435 via 441 and the sequence repeated until flame is indicated to be present or 90 seconds passes at 442 in which case the flameout message 443 is displayed and the instrument is placed in a manual lockout state at 444 which requires the attention of service personnel.

Once the burner flame is stabilized and the startup logic flow exits at 437, the control returns again to the main routine which thereafter transfers control sequentially to the other tasks as controlled by the real time interrupt subroutine 409. The real time interrupt times out once every second as shown in FIG. 10a and controls the timing of the running of each of the other tasks. That routine also keeps the date and the time current.

Figure 14A:
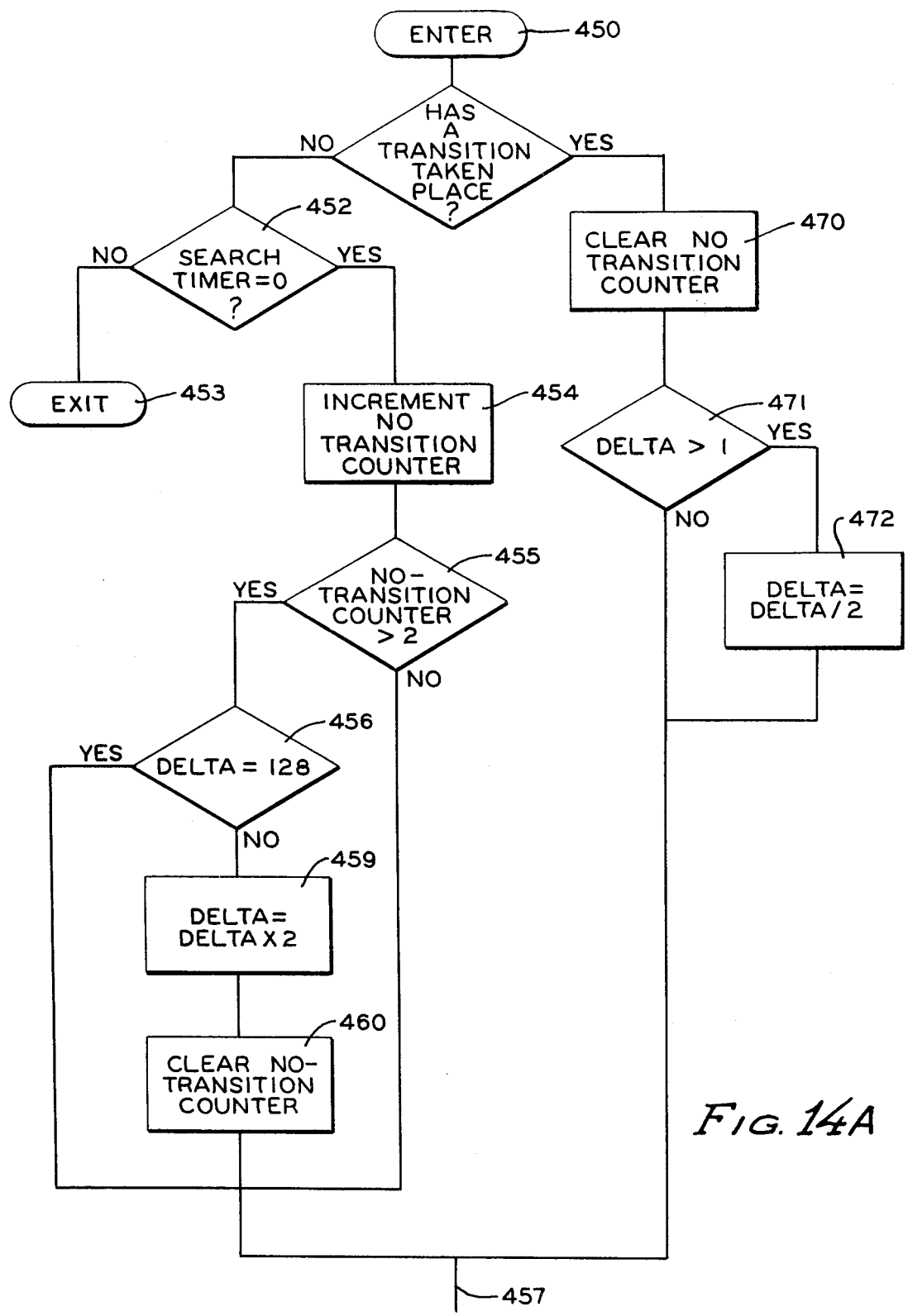
FIG. 14, including Parts 14A and 14B is a logic diagram for the search task of FIG. 11.
Figure 14B:
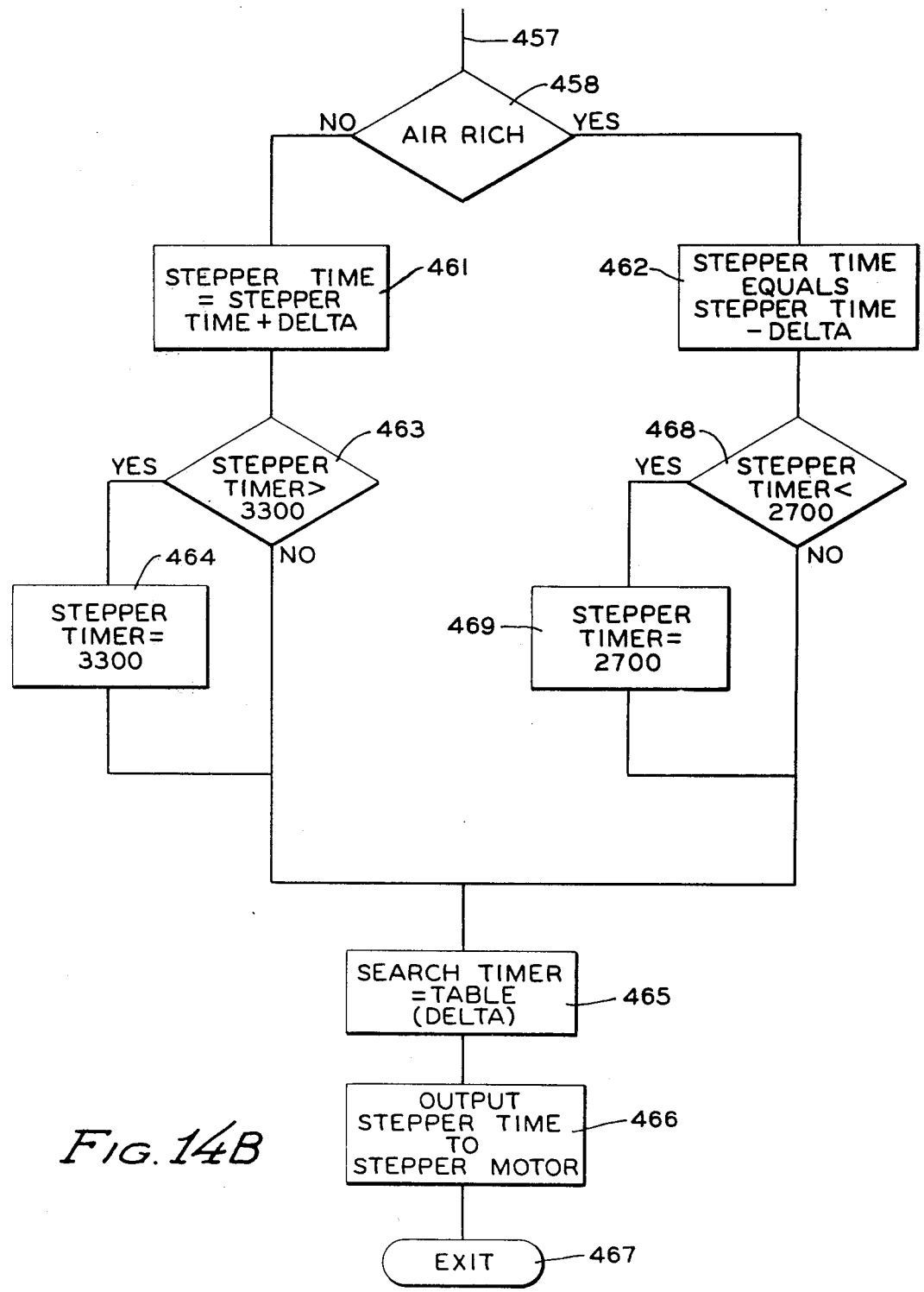

The first of these tasks is the `call search task 407 which is shown in detail in FIG. 14. Thus, when the real time interrupt indicates that the search task should be called, the logic flow enters on 450 and the search task is begun. It is the search task that attempts to find the point of the stoichiometry mixture ratio and thereafter to track this ratio as closely as possible such that the sample burner mixture is maintained as close as possible to the stoichiometry point of the mixture of interest. As previously described, the $ZrO_2$ sensor provides a continuous feedback signal dependent upon the partial pressure of oxygen in the sample combustion chamber. This feedback signal is continuously compared to a threshold or set point in the threshold detector. Thus, the first inquiry made by the search task at 451 is whether in fact a transition has taken place, i.e. whether the $ZrO_2$ feedback has crossed the threshold. If not, the status of the search timer is checked at 452 and if this is not timed out the logic flow exits at 453 until the next time the search task is called by the real time interrupt.

If no transition has taken place but the search timer has timed out, this indicates by the state of the threshold indicator that the mixture is either on the rich or lean side of the threshold or transition point and therefore a change in the ratio is indicated if it is to approach the stoichiometric or transition point. This is accomplished by first incrementing a no transition counter 454 which indicates that no transition has taken place for a given number of counts. If that given number is greater than 2 as at 455, the value of delta is checked. Delta is equal to a given amount related to the amount by which the frequency of the stepping motor is changed to speed up or slow down and thereby change the air-fuel ratio at the sample burner. The maximum delta is given a value of 128. Thus, if the no transition counter has a value greater than 2 and the value of delta at 456 is equal to 128 which is the maximum, the signal goes via 457 to 458 where a determination as to whether the mixture is air rich or not depending on the state of the threshold detector is made. If, however, delta does not equal the maximum of 128 at 456, delta is doubled at 459 and the increment no transition counter 454 is cleared at 460 and the logic flow proceeds to 458. If the no transition counter has not yet reached a value greater than 2, the logic flow also proceeds to 458. After the decision at 458, the stepper time is either increased or decreased by the amount delta 461 and 462, respectively, depending on whether the mixture is determined to be air rich or not. Of course, by slowing down the stepper time, the frequency of steps is decreased and the speed of rotation of the rotor is decreased thereby leaning the mixture.

Thus, if the decision at 458 was that the mixture was fuel rich, the stepper time is increased by the amount delta thus slowing down the rotation by a given related amount. The stepper frequency is then compared with a maximum stepper time or slower rotor speed of 3300 microseconds. If the speed is greater than this at 464, it is reset to 3300 microseconds and the search task outputs a new frequency at 465 and 466 exiting at 467. Likewise, if the mixture is determined to be air rich, the stepper timer is compared at 468 which its slowest allowable speed and reset if necessary at 469 with the output again being modulated at 465 and 466.

In similar fashion, if the search task first indicates that in fact a transition has occurred, then the no transition counter 455 is cleared at 470 and the value of delta checked at 471. If delta is greater than 1, which is the minimum delta, then the inverse of the reaction at 459 occurs and the value of delta is halved at 47 with the logic flow then proceeding to 458 where the same sequence just described occurs. The value of delta may vary from 1 to 128 and the purpose of doubling and having delta is required is to attempt to speed the search operation in an effort to bracket the transition point such that close tracking of the stoichiometric air-fuel ratio can be accomplished. As can be seen from the search task of FIG. 14, if delta continually equals 1 and a transition takes place upon each search, a very low modulation about the stoichiometric point occurs and the system is truly tracking correctly, assuming that the mixture itself does not change. The search task is normally called about every two seconds which gives some delay time for the $ZrO_2$ sensor to stabilize after each change. After the search task logic flow exits at 467, control is returned to the main routine as interfaced by the real time interrupt. The rest of the main routine is concerned with a series of other tasks which are interfaced with the main routine by timers, which, upon timing out, enable the other tasks to gain control and be executed.

In this manner, if the calibration timer is equal to 0 when the logic flow is sequenced at 480, the calibration task 403 will be called. Other such timers include data logger timer 481, display timer 482, read temperature timer 483, and two panel initiated buttons including a calibrate button and a print button 484 and 485, respectively.

Figure 15:
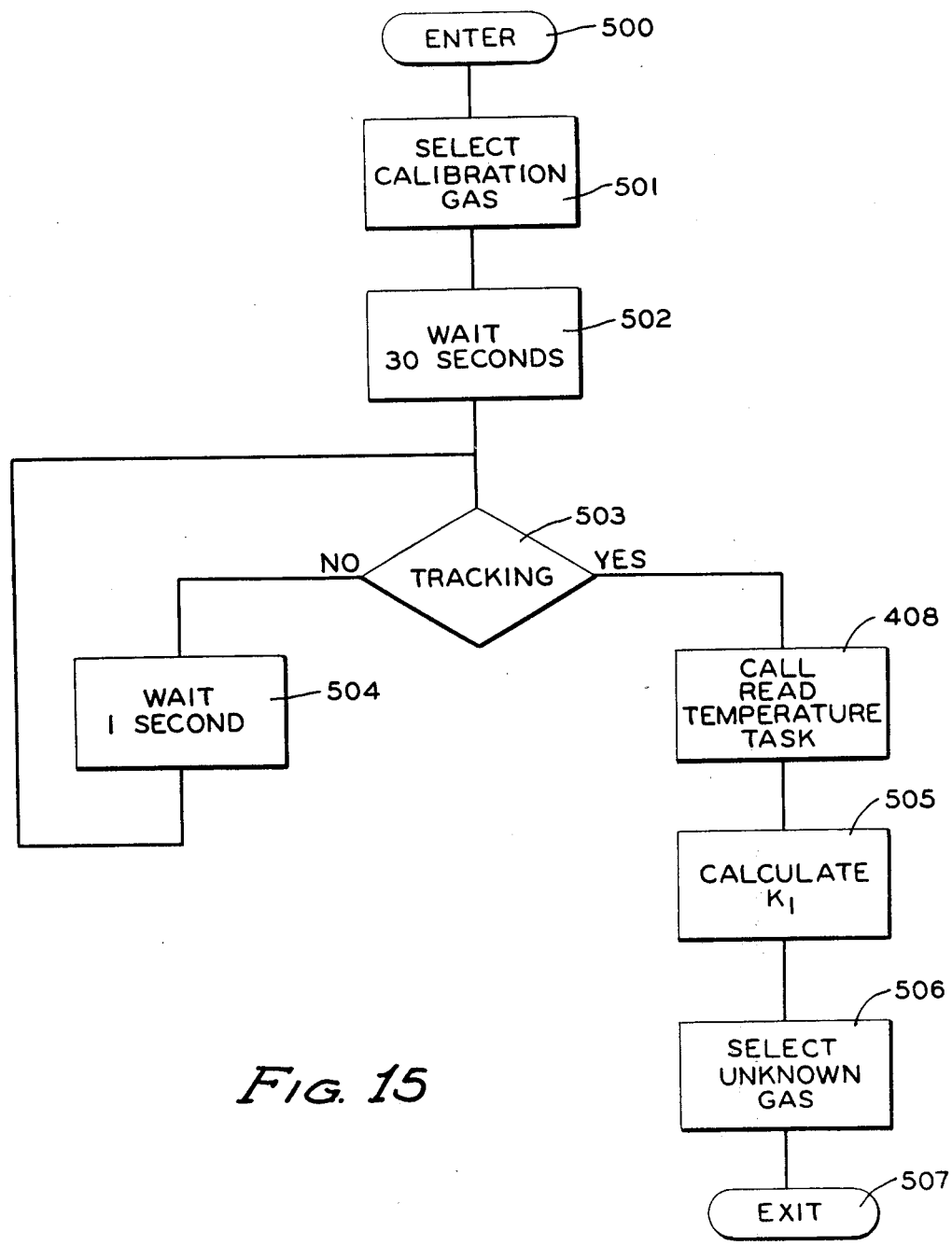
FIG. 15 is a logic diagram for the calibrate task of FIG. 11.

Assuming that the calibration timer is timed out, or that the push button 484 has been pushed, the main routine relinquishes control to the calibration task of FIG. 15. In this task, the logic flow enters as at 500 and selects the calibration gas at 501. This causes the three-way inlet valve to switch from sample gas or gas of interest to calibration gas as the fuel gas. After a 30-second delay to allow the burner to stabilize at 502, the system is checked as to whether it is tracking at 503 prior to search routine 407. If not, this is checked continually on a one-second delay as at 504 until tracking occurs at which time the read temperature fask 408 (discussed below) is called. Based on the output of the read temperature task 408, the constant $K_1$ utilized in the BTU calculation as described is recalculated utilizing any necessary temperature correction as at 505 and the inlet valve is again switched back to the sample or unknown gas of interest as at 506 and the logic flow exits at 507 returning control back to the main task. The method of correction for temperature is discussed below in relation to the read temperature task in FIG. 17. The calibration timer is reloaded at 487 and calibration will not occur automatically until the calibration timer again times out. The calibration timers is normally set for a period of up to 12 hours such that if calibration is successful, it occurs only rarely in the operation of a device.

When the data logger timer 431 times out, the data logger task 404 is called to cause the data at 487 to be printed and thereafter the data logger timer is reloaded at 488. This routine allows certain data to be periodically printed to monitor the operation of the system.

In a like manner, the display task 405 is called and, as seen in FIG. 16, logic flow enters at 510 and asks the status of the time and date thumb wheels as at 511. Thus, the display can update the time and date as at 513 and 514, calculate the BTU or heating value of the fuel from the floating point mathematics as at 515, and display the results as at 516. Returning to the main routine, again the display timer is reloaded as at 489. In a like manner, the main task executes the read temperature task 408. This task is shown in detail in FIG. 17. The logic flow enters at 520, and the input from the calibration resistor which is the standard against which the temperature sensor is compared is called at 521. The voltage-to-frequency routine is called at 522 which outputs a frequency signal based on the calibration resistor. In a similar manner, at 523–526, frequency signals are generated for the air temperature sensor and the mixture temperature sensor and from these at 527 and 528 the resistance of the air sensor and mixture sensor can be calculated and the air and mixture temperature is derived at 529 and 530.

After completing one cycle of the main routine, the routine is returned to being timing through the tasks again as at 490. Thus, the routine begins all over again and continues to continually go through the various routines as determined by the real time interrupt and the various timers associated with each routine.

The mechanical components of the systems of FIGS. 2 and 3 may be any conventional components which meet the requirements of the system. These include the pressure regulators, temperature sensors, flame safeguards, safety and ignition systems, and burners. These are all conventional items available from a variety of manufacturers.

In the embodiment of FIG. 2, the stepping motor used in one successful embodiment was a 6000 series SLO-SYN stepping motor available from the Superior Electric Company of Bristol, Connecticut. These motors have a 1.8° step angle or a total of 200 steps per revolution of the shaft. Thus, each control input can step the motor as little as 1.8°. The flexible coupling 105 used in one successful embodiment in conjunction with the stepping motor was an MCA 100 HELI-CAL flexible coupling manufactured by the HELICAL Products Company, Inc. of Santa Maria, California.

It can readily be seen from the above description that the several proportioning systems which have been described in accordance with the heat content measuring system of the present invention may have many applications elsewhere. These proportioning systems have characteristics that make them quite useful for the accurate mixing of all types of gases and even liquids in association with other systems.

As can be seen from the above description, the heat content measuring system of the present invention including the several alternate proportioning systems provides an effective, simple, and accurate system for determining the heat content of gaseous hydrocarbon fuels. Results utilizing the invention indicate that very high accuracies can be obtained readily.

The embodiments of the invention in which an exclusive property or right is claimed are defined as follows:

1. Apparatus for establishing a mixture of interest of known volumetric proportions comprising:
   a rotary proportioning system comprising at least:
   a first inlet means adapted to connect to a source of first component to be mixed;
   second inlet means adapted to connect to a source of a second component to be mixed;
   first outlet means for discharging to effluent;
   second outlet means for discharging the mixture of interest;
   rotatable member, said rotatable member being adapted to be continuously rotated in a desire direction and provided with a plurality of fixed hollow volumes having open accesses at the extremes thereof such that upon rotation of said rotatable member each of said volumes is sequentially connected between said first inlet and said first outlet and said second inlet and said second outlet, said rotatable member further comprising a cylinder provided with a series of spaced radially distributed openings therethrough forming an annular pattern; and
   wherein said apparatus further comprises:
   first non-rotating member for containing said first and said second inlet means;
   wherein said first inlet means further comprises a partially annular first inlet groove in said non-rotating member juxtaposed to and communicating with the inlet accesses of the openings in said rotatable member located opposite said groove; and
   wherein said second inlet means further comprises a partially annular second inlet groove in said non-rotating member spaced from said first groove and relatively longer than said first groove also being juxtaposed to and in communication with the inlet accesses of said openings in said rotatable member located opposite said second groove; and
   second non-rotating member containing said first and second outlet means comprising counterpart first and second outlet grooves symmetrical to and aligned with said first and second inlet grooves, said outlet grooves being juxtaposed to and in communication with the outlet accesses of said openings in said rotatable member opposite them; and
   wherein said first and second inlet grooves further respectively are in communication with said source of said first component and said source of said second component; and
   wherein said first outlet groove is in communication with and effluent conduct means and said second outlet groove is in communication with a conduit means for conveying the mixture of interest; and
   means for rotating said rotatable member.

2. Apparatus for establishing a mixture of interest of known volumetric porportions comprising:
   a rotary proportioning system comprising at least:
   a first inlet means adapted to connect to a source of a first component to be mixed;
   second inlet means adapted to connect to a source of a second component to be mixed;
   first outlet means for discharging to effluent;
   second outlet means for discharging the mixture of interest;
   rotatable member, said rotatable member being adapted to be continuously rotated in a desired direction and provided with a plurality of fixed hollow volumes having open accesses at the extremes thereof such that upon rotation of said rotatable member each of said volume is sequentially connected between first inlet and said first outlet and said second inlet and said second outlet, said rotatable member further comprising a cylinder provided with dual inner and outer series of spaced radially distributed openings forming a symmetrical pattern such that each inner opening is paired with a corresponding outer opening and hollow grooves connecting the bottoms of the holes in each pair forming U-shaped passages thereby; and
   wherein said apparatus further comprises a non-rotating member further comprising;
   inner and outer pairs of parallel fixed partially annular grooves juxtaposed to and aligned with said inner and outer series of openings, each of said pairs of grooves comprising a shorter and a longer groove spaced apart and wherein the two shorter and two longer grooves are in radial alignment;
   wherein one of said shorter grooves connects to said source of said first component and the other of said shorter grooves connects to an effluent outlet; and
   wherein one of said longer grooves is connected with said slource of said second component and the other of said longer grooves is connected with an outlet for said mixture of interest; and
   means for rotating said rotatable member.

3. The apparatus of either of claims 1 or 2 further comprising sealing means between said rotating member and each of said non-rotating members to prevent internal crossflow in said apparatus and leakage from said apparatus.

4. The apparatus of either of claims 1 or 2 wherein the relation between said first and second inlet means and said first and second outlet means is such that flow of said first component is continually maintained to said first outlet and flow of said second component is continually maintained to said second outlet regardless of the rotational position of the rotatable member.

5. The apparatus of claims 1 or 2 wherein said means for rotating said rotatable member is a stepping motor.

6. The apparatus of claim 5 further comprising means for controlling and varying the speed of said motor.

7. The apparatus of either of claims 1 or 2 wherein said inlet and outlet connections to said sources of first and second components and said outlet connections to effluent and said mixture comprise openings connecting said grooves and wherein the corresponding openings connecting said inlet grooves and said outlet grooves are located at opposite extremes of said slots such that the contents of the grooves also tends to flow along said slots in traversing the system.

8. The apparatus of either of claims 1 or 2 wherein said inlet and outlet connections to said sources of first and second components and said outlet connections to effluent and said mixture comprise openings connecting said grooves and wherein the corresponding openings connecting said inlet grooves and said outlet grooves are located at opposite extremes of said slots such that the contents of the slots also tends to flow along said slots in traversing the system.

9. The apparatus of either claims 1 or 2 wherein the disposition of said inlet and outlet openings accessing said grooves relative to the direction of rotation of said rotatable member is such that the first component tends to flow along the inlet groove in a direction opposite to the rotation of the rotatable member and the second component tends to flow in the same direction as the rotation of the rotatable member.

10. The apparatus of either of claims 1 or 2 wherein the openings in the rotatable member are slots.

11. The apparatus of either of claims 1 or 2 wherein the openings in the rotatable member are cylindrical holes.

12. Apparatus for establishing a mixture of interest of known volumetric proportions comprising:
   a rotary proportioning system comprising at least:
   a first inlet means adapted to connect to a source of a first component to be mixed;
   second inlet means adapted to connect to a source of a second component to be mixed;
   first outlet means for discharging to effluent;
   second outlet means for discharging the mixture of interest;
   rotatable member, said rotatable member being adapted to be continuously rotated in a desired direction and provided with a plurality of fixed hollow volumes having open accesses at the extremes thereof such that upon rotation of said rotatable member each of said volumes is sequentially connected between said first inlet and said first outlet and said second inlet and said second outlet;
   means for rotating said rotatable member; and wherein the relation between said first and second inlet means and said first and second outlet means is such that flow of said first component is continually maintained to said first outlet and flow of said second component is continually maintained to said second outlet regardless of the rotational position of the rotatable member.

13. The apparatus of any of claims 1, 2 or 12 comprising additional inlets and outlets for mixing additional pairs of fluids.

* * * * *